United States Patent [19]

Mulvihill et al.

[11] Patent Number: 5,869,609
[45] Date of Patent: Feb. 9, 1999

[54] G PROTEIN COUPLED GLUTAMATE RECEPTORS

[75] Inventors: Eileen Ranae Mulvihill; Frederick Stamner Hagen; Khaled M. Houamed; Wolfhard Almers, all of Seattle, Wash.

[73] Assignees: Zymogenetics, Inc.; The Board of Regents of the University of Washington, both of Seattle, Wash.

[21] Appl. No.: 465,157

[22] Filed: Jun. 5, 1995

Related U.S. Application Data

[60] Division of Ser. No. 101,676, Aug. 3, 1993, abandoned, which is a continuation-in-part of Ser. No. 648,481, Jan. 30, 1991, abandoned, which is a continuation-in-part of Ser. No. 626,806, Dec. 12, 1990, abandoned.

[51] Int. Cl.$^6$ ........................ C07K 14/705; G01N 33/53; C12P 21/02; C12N 15/12
[52] U.S. Cl. ........................... 530/350; 435/72; 435/69.1; 536/23.5
[58] Field of Search .............................. 530/350; 435/7.2, 435/69.1; 536/23.5

[56] References Cited

U.S. PATENT DOCUMENTS

| | | | |
|---|---|---|---|
| 4,859,609 | 8/1989 | Dull et al. | 436/501 |
| 5,385,831 | 1/1995 | Mulvihill et al. | . |

FOREIGN PATENT DOCUMENTS

| | | |
|---|---|---|
| 569240 | 11/1993 | European Pat. Off. . |
| 600278 | 6/1994 | European Pat. Off. . |

OTHER PUBLICATIONS

Gunderson et al., "Glutamate and Kainate Receptors Induced by Rat Brain Messenger RNA in Xenopus Oocytes," *Proc. Royal Soc. London Series B* 221:127–143, (1984).
Houamed, et al., "Cloning, Expression, and Gene Structure of a G Protein–Coupled Glutamate Receptor from Rat Brain", *Science*, 252:1318–1321.
Sladeczek et al., "Glutamate Stimulates Inositol Phosphate Formation in Striatal Neurones," *Nature* 317:717–719, (1985).
Dascal et al., "Involvement of a GTP–Binding Protein in Mediation of Serotonin and Acetylcholine Responses in Xenopus Oocytes Injected with Rat Brain Messenger RNA," *Mol. Brain Res.* 1:201–209, (1986).
Verdoorn et al., Rat Brain N–Methyl–D–Aspartate Receptors Expressed in Xenopus Oocytes, *Science* 238:1114–1116, (1987).
Recasens et al., "Characterization of Subtypes of Excitatory Amino Acid Receptors Involved in the Stimulation of Inositol Phosphate Synthesis in Rat Brain Synaptoneurosomes," *Eur. J. Pharmacology* 141:87–93, (1987).
Sugiyama et al., "A New Type of Glutamate Receptor Linked to Inositol Phospholipid Metabolism," *Nature* 325:531–533, (1987).
Takahashi et al., "Rat Brain Serotonin Receptors in Xenopus Oocytes are Coupled by Intracellular Calcium to Endogenous Channels," *Proc. Natl. Acad. Sci. USA.*, 84:5063–5067 (1987).
Hirono et al., "Characterization of Glutamate Receptors Induced in Xenopus Oocytes after Injection of Rat Brain mRNA," *Neurosci. Res.*, 6:106–114, (1988).
Verdoorn and Dingledine, "Excitatory Amino Acid Receptors Expressed in Xenopus Oocytes: Agonist Pharmacology," *Mol. Pharmacol.* 34:298–307, (1988).
Snutch, "The Use of Xenopus Oocytes to Probe Synaptic Communication," *Trends In Neurosci* 6:250–256, (1988).
Fong et al., "Properties of Two Classes of Rat Brain Acidic Amino Acid Receptors Induced by Distinct mRNA Populations in Xenopus Oocytes," *Synapse* 2:657–665, (1988).
Recasens et al., "A New Quisqualate Receptor Subtype (sAA$_2$) Responsible for the Glutamate–Induced Inositol Phosphate Formation in Rat Brain Synaptoneurosomes," *Neurochem. Int.* 13:463–467 (1988).
Oosawa et al., "Rat Brain Glutamate Receptors Activate Chloride Channels in Xenopus Oocytes Coupled by Inositol Trisphosphate and Ca2+," *J. Physiol.*, 408:223–232 (1989).
Horikoshi et al., "Regional Distribution of Metabotropic Glutamate Response in the Rat Brain using Xenopus Oocytes," *Neurosci. Lett.* 105:340–343, (1989).
Hollmann et al., "Cloning by Functional Expression of a Member of the Glutamate Receptor Family," *Nature* 342:643–648, (1989).
Sugiyama et al., "Glutamate Receptor Subtypes May be Classified into Two Major Categories: A Study on Xenopus Oocytes Injected with Rat Brain mRNA," *Neuron* 3:129–132, (1989).
Moriarty and Landau, Xenopus Oocyte as Model System to Study Receptor Coupling to Phospholipase C, *G Proteins*, Academic Press, N.Y., pp. 479–501 (1990).
Sommer et al., "Flip and Flop: A Cell–Specific Functional Switch in Glutamate–Operated Channels of the CNS," *Science* 249:1580–1585, (1990).
Schoepp et al., "Pharmacological and Functional Characteristics of Metabotropic Excitatory Amino Acid Receptors," *Trends Pharm. Sci.*, 11:508–515 (1990).
Masu et al., "Sequence and Expression of a Metabotropic Glutamate Receptor," *Nature* 349:760–765 (Feb. 28, 1991).
Watson et al., "The G–Protein Linked Receptor Facts Book," Academic Press (1994).

*Primary Examiner*—Stephen Walsh
*Assistant Examiner*—Daryl A. Basham
*Attorney, Agent, or Firm*—Townsend & Townsend & Crew LLP

[57] ABSTRACT

Mammalian G protein coupled glutamate receptors are identified, isolated and purified. The receptors have been cloned, sequenced and expressed by recombinant means. The receptors and antibodies thereby may be used to identify agonists and antagonists of G protein coupled glutamate receptor mediated neuronal excitation, as well as in methods of diagnosis.

6 Claims, 14 Drawing Sheets

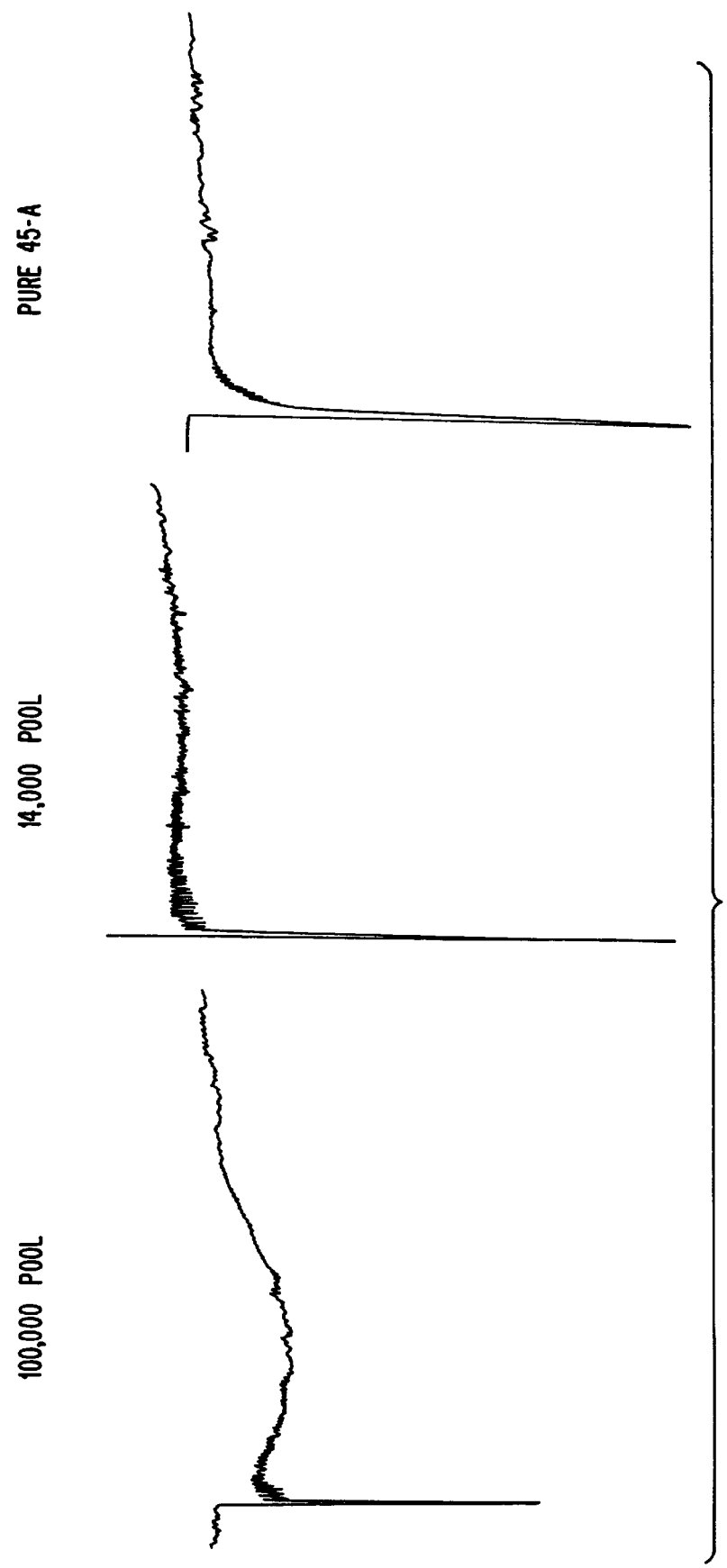

```
                                                                    60
CCGAGAACGG CTGCAGTCCT CTGACCTGAG ACCAATAGCT GTGTCTACCC GGACTCAGCG

120
TCCAGCTCAC CGCCACTAAC GCGCCGCGCA TTGGACACCT GATCCACACA CCTTCGGGCA

180
CCAGTGAAAA ACCGCGACTT GATTTCTGG AAGAACGCCC CCAGGGTGTG GGAGCGGTCG

240
TGGAGGACCA GCAGGAGGAA GCGGAGGGGA GAGGGGCAGT AGTGGAGGCA GAGAAAGCGT

300
TGAACCAGCT GTGTTGGCCG AAGGCACGAA ACGGCAAAAG GCAGCGGTGA GCATCTGTGT

360
GGTTCCCGCT GGGAACCTGC AGGCAGGACC GGCGTGGGAA CGTGGCTGGC CCGCGGTGGA

409
CCGCGTCTTC GCCACA ATG GTC CGG CTC CTC TTG ATT TTC TTC CCA ATG
                   Met Val Arg Leu Leu Leu Ile Phe Phe Pro Met
                    1               5                      10

457
ATC TTT TTG GAG ATG TCC ATT TTG CCC AGG ATG CCT GAC AGA AAA GTA
Ile Phe Leu Glu Met Ser Ile Leu Pro Arg Met Pro Asp Arg Lys Val
                 15                  20                  25

505
TTG CTG GCA GGT GCC TCG TCC CAG CGC TCC GTG GCG AGA ATG GAC GGA
Leu Leu Ala Gly Ala Ser Ser Gln Arg Ser Val Ala Arg Met Asp Gly
             30                  35                  40

553
GAT GTC ATC ATC GGA GCC CTC TTC TCA GTC CAT CAC CAG CCT CCA GCC
Asp Val Ile Ile Gly Ala Leu Phe Ser Val His His Gln Pro Pro Ala
         45                  50                  55

601
GAG AAG GTA CCC GAA AGG AAG TGT GGG GAG ATC AGG GAA CAG TAT GGT
Glu Lys Val Pro Glu Arg Lys Cys Gly Glu Ile Arg Glu Gln Tyr Gly
 60                  65                  70                  75

649
ATC CAG AGG GTG GAG GCC ATG TTC CAC ACG TTG GAT AAG ATT AAC GCG
Ile Gln Arg Val Glu Ala Met Phe His Thr Leu Asp Lys Ile Asn Ala
                 80                  85                  90

697
GAC CCG GTG CTC CTG CCC AAC ATC ACT CTG GGC AGT GAG ATC CGG GAC
Asp Pro Val Leu Leu Pro Asn Ile Thr Leu Gly Ser Glu Ile Arg Asp
             95                 100                 105

745
TCC TGC TGG CAC TCT TCA GTG GCT CTC GAA CAG AGC ATC GAA TTC ATC
Ser Cys Trp His Ser Ser Val Ala Leu Glu Gln Ser Ile Glu Phe Ile
         110                 115                 120
```

*FIG. 5A.*

```
                                                              793
AGA GAC TCC CTG ATT TCC ATC CGA GAT GAG AAG GAT GGG CTG AAC CGA
Arg Asp Ser Leu Ile Ser Ile Arg Asp Glu Lys Asp Gly Leu Asn Arg
    125             130                 135

841
TGC CTG CCT GAT GGC CAG ACC CTG CCC CCT GGC AGG ACT AAG AAG CCT
Cys Leu Pro Asp Gly Gln Thr Leu Pro Pro Gly Arg Thr Lys Lys Pro
140             145                 150                      155

889
ATT GCT GGA GTG ATC GGC CCT GGC TCC AGC TCT GTG GCC ATT CAA GTC
Ile Ala Gly Val Ile Gly Pro Gly Ser Ser Ser Val Ala Ile Gln Val
                160             165                 170

937
CAG AAT CTT CTC CAG CTG TTC GAC ATC CCA CAG ATC GCC TAT TCT GCC
Gln Asn Leu Leu Gln Leu Phe Asp Ile Pro Gln Ile Ala Tyr Ser Ala
            175             180                 185

985
ACA AGC ATA GAC CTG AGT GAC AAA ACT TTG TAC AAA TAC TTC CTG AGG
Thr Ser Ile Asp Leu Ser Asp Lys Thr Leu Tyr Lys Tyr Phe Leu Arg
        190             195                 200

1033
GTG GTC CCT TCT GAC ACT TTG CAG GCA AGG GCG ATG CTC GAC ATA GTC
Val Val Pro Ser Asp Thr Leu Gln Ala Arg Ala Met Leu Asp Ile Val
    205             210                 215

1081
AAG CGT TAC AAC TGG ACC TAT GTC TCA GCA GTC CAC ACA GAA GGG AAT
Lys Arg Tyr Asn Trp Thr Tyr Val Ser Ala Val His Thr Glu Gly Asn
220             225                 230                     235

1129
TAC GGC GAG AGT GGA ATG GAT GCT TTC AAA GAA CTG GCT GCC CAG GAA
Tyr Gly Glu Ser Gly Met Asp Ala Phe Lys Glu Leu Ala Ala Gln Glu
                240             245                 250

1177
GGC CTC TGC ATC GCA CAC TCG GAC AAA ATC TAC AGC AAT GCT GGC GAG
Gly Leu Cys Ile Ala His Ser Asp Lys Ile Tyr Ser Asn Ala Gly Glu
            255             260                 265

1225
AAG AGC TTT GAC CGG CTC CTG CGT AAA CTC CGG GAG CGG CTT CCC AAG
Lys Ser Phe Asp Arg Leu Leu Arg Lys Leu Arg Glu Arg Leu Pro Lys
        270             275                 280

1273
GCC AGG GTT GTG GTC TGC TTC TGC GAG GGC ATG ACA GTG CGG GGC TTA
Ala Arg Val Val Val Cys Phe Cys Glu Gly Met Thr Val Arg Gly Leu
    285             290                 295
```

FIG. 5B.

```
                                                                      1321
CTG AGT GCC ATG CGC CGC CTG GGC GTC GTG GGC GAG TTC TCA CTC ATT
Leu Ser Ala Met Arg Arg Leu Gly Val Val Gly Glu Phe Ser Leu Ile
300             305             310             315

1369
GGA AGT GAT GGA TGG GCA GAC AGA GAT GAA GTC ATC GAA GGC TAT GAG
Gly Ser Asp Gly Trp Ala Asp Arg Asp Glu Val Ile Glu Gly Tyr Glu
                320             325             330

1417
GTG GAA GCC AAC GGA GGG ATC ACA ATA AAG CTT CAG TCT CCA GAG GTC
Val Glu Ala Asn Gly Gly Ile Thr Ile Lys Leu Gln Ser Pro Glu Val
            335             340             345

1465
AGG TCA TTT GAT GAC TAC TTC CTG AAG CTG AGG CTG GAC ACC AAC ACA
Arg Ser Phe Asp Asp Tyr Phe Leu Lys Leu Arg Leu Asp Thr Asn Thr
        350             355             360

1513
AGG AAT CCT TGG TTC CCT GAG TTC TGG CAA CAT CGC TTC CAG TGT CGC
Arg Asn Pro Trp Phe Pro Glu Phe Trp Gln His Arg Phe Gln Cys Arg
    365             370             375

1561
CTA CCT GGA CAC CTC TTG GAA AAC CCC AAC TTT AAG AAA GTG TGC ACA
Leu Pro Gly His Leu Leu Glu Asn Pro Asn Phe Lys Lys Val Cys Thr
380             385             390             395

1609
GGA AAT GAA AGC TTG GAA GAA AAC TAT GTC CAG GAC AGC AAA ATG GGA
Gly Asn Glu Ser Leu Glu Glu Asn Tyr Val Gln Asp Ser Lys Met Gly
                400             405             410

1657
TTT GTC ATC AAT GCC ATC TAT GCC ATG GCA CAT GGG CTG CAG AAC ATG
Phe Val Ile Asn Ala Ile Tyr Ala Met Ala His Gly Leu Gln Asn Met
            415             420             425

1705
CAC CAT GCT CTG TGT CCC GGC CAT GTG GGC CTG TGT GAT GCT ATG AAA
His His Ala Leu Cys Pro Gly His Val Gly Leu Cys Asp Ala Met Lys
        430             435             440

1753
CCC ATT GAT GGC AGG AAG CTC CTG GAT TTC CTC ATC AAA TCC TCT TTT
Pro Ile Asp Gly Arg Lys Leu Leu Asp Phe Leu Ile Lys Ser Ser Phe
    445             450             455

1801
GTC GGA GTG TCT GGA GAG GAG GTG TGG TTC GAT GAG AAG GGG GAT GCT
Val Gly Val Ser Gly Glu Glu Val Trp Phe Asp Glu Lys Gly Asp Ala
460             465             470             475
```

*FIG. 5C.*

```
                                                                    1849
CCC GGA AGG TAT GAC ATT ATG AAT CTG CAG TAC ACA GAA GCT AAT CGC
Pro Gly Arg Tyr Asp Ile Met Asn Leu Gln Tyr Thr Glu Ala Asn Arg
                480                 485                 490

1897
TAT GAC TAT GTC CAC GTG GGG ACC TGG CAT GAA GGA GTG CTG AAT ATT
Tyr Asp Tyr Val His Val Gly Thr Trp His Glu Gly Val Leu Asn Ile
                495                 500                 505

1945
GAT GAT TAC AAA ATC CAG ATG AAC AAA AGC GGA ATG GTA CGA TCT GTG
Asp Asp Tyr Lys Ile Gln Met Asn Lys Ser Gly Met Val Arg Ser Val
                510                 515                 520

1993
TGC AGT GAG CCT TGC TTA AAG GGT CAG ATT AAG GTC ATA CGG AAA GGA
Cys Ser Glu Pro Cys Leu Lys Gly Gln Ile Lys Val Ile Arg Lys Gly
    525                 530                 535

2041
GAA GTG AGC TGC TGC TGG ATC TGC ACG GCC TGC AAA GAG AAT GAG TTT
Glu Val Ser Cys Cys Trp Ile Cys Thr Ala Cys Lys Glu Asn Glu Phe
540                 545                 550                 555

2089
GTG CAG GAC GAG TTC ACC TGC AGA GCC TGT GAC CTG GGG TGG TGG CCC
Val Gln Asp Glu Phe Thr Cys Arg Ala Cys Asp Leu Gly Trp Trp Pro
                560                 565                 570

2137
AAC GCA GAG CTC ACA GGC TGT GAG CCC ATT CCT GTC CGT TAT CTT GAG
Asn Ala Glu Leu Thr Gly Cys Glu Pro Ile Pro Val Arg Tyr Leu Glu
                575                 580                 585

2185
TGG AGT GAC ATA GAA TCT ATC ATA GCC ATC GCC TTT TCT TGC CTG GGC
Trp Ser Asp Ile Glu Ser Ile Ile Ala Ile Ala Phe Ser Cys Leu Gly
                590                 595                 600

2233
ATC CTC GTG ACG CTG TTT GTC ACC CTC ATC TTC GTT CTG TAC CGG GAC
Ile Leu Val Thr Leu Phe Val Thr Leu Ile Phe Val Leu Tyr Arg Asp
            605                 610                 615

2281
ACA CCC GTG GTC AAA TCC TCC AGT AGG GAG CTC TGC TAT ATT ATT CTG
Thr Pro Val Val Lys Ser Ser Ser Arg Glu Leu Cys Tyr Ile Ile Leu
620                 625                 630                 635

2329
GCT GGT ATT TTC CTC GGC TAT GTG TGC CCT TTC ACC CTC ATC GCC AAA
Ala Gly Ile Phe Leu Gly Tyr Val Cys Pro Phe Thr Leu Ile Ala Lys
                640                 645                 650
```

*FIG. 5D.*

```
                                                                        2377
CCT ACT ACC ACA TCC TGC TAC CTC CAG CGC CTC CTA GTT GGC CTC TCT
Pro Thr Thr Thr Ser Cys Tyr Leu Gln Arg Leu Leu Val Gly Leu Ser
            655             660             665

2425
TCT GCC ATG TGC TAC TCT GCT TTA GTG ACC AAA ACC AAT CGT ATT GCA
Ser Ala Met Cys Tyr Ser Ala Leu Val Thr Lys Thr Asn Arg Ile Ala
        670             675             680

2473
CGC ATC CTG GCT GGC AGC AAG AAG AAG ATC TGC ACC CGG AAG CCC AGA
Arg Ile Leu Ala Gly Ser Lys Lys Lys Ile Cys Thr Arg Lys Pro Arg
    685             690             695

2521
TTC ATG AGC GCT TGG GCC CAA GTG ATC ATA GCC TCC ATT CTG ATT AGT
Phe Met Ser Ala Trp Ala Gln Val Ile Ile Ala Ser Ile Leu Ile Ser
700             705             710             715

2569
GTA CAG CTA ACA CTA GTG GTG ACC TTG ATC ATC ATG GAG CCT CCC ATG
Val Gln Leu Thr Leu Val Val Thr Leu Ile Ile Met Glu Pro Pro Met
            720             725             730

2617
CCC ATT TTG TCC TAC CCG AGT ATC AAG GAA GTC TAC CTT ATC TGC AAT
Pro Ile Leu Ser Tyr Pro Ser Ile Lys Glu Val Tyr Leu Ile Cys Asn
        735             740             745

2665
ACC AGC AAC CTG GGT GTA GTG GCC CCT GTG GGT TAC AAT GGA CTC CTC
Thr Ser Asn Leu Gly Val Val Ala Pro Val Gly Tyr Asn Gly Leu Leu
    750             755             760

2713
ATC ATG AGC TGT ACC TAC TAT GCC TTC AAG ACC CGC AAC GTG CCG GCC
Ile Met Ser Cys Thr Tyr Tyr Ala Phe Lys Thr Arg Asn Val Pro Ala
765             770             775

2761
AAC TTC AAT GAG GCT AAA TAC ATC GCC TTC ACC ATG TAC ACT ACC TGC
Asn Phe Asn Glu Ala Lys Tyr Ile Ala Phe Thr Met Tyr Thr Thr Cys
780             785             790             795

2809
ATC ATC TGG CTG GCT TTC GTT CCC ATT TAC TTT GGG AGC AAC TAC AAG
Ile Ile Trp Leu Ala Phe Val Pro Ile Tyr Phe Gly Ser Asn Tyr Lys
        800             805             810

2857
ATC ATC ACT ACC TGC TTC GCG GTG AGC CTC AGT GTG ACG GTG GCC CTG
Ile Ile Thr Thr Cys Phe Ala Val Ser Leu Ser Val Thr Val Ala Leu
            815             820             825
```

FIG. 5E.

```
                                                              2905
GGG TGC ATG TTT ACT CCG AAG ATG TAC ATC ATC ATT GCC AAA CCT GAG
Gly Cys Met Phe Thr Pro Lys Met Tyr Ile Ile Ile Ala Lys Pro Glu
        830                 835                 840

2953
AGG AAC GTC CGC AGT GCC TTC ACG ACC TCT GAT GTT GTC CGC ATG CAC
Arg Asn Val Arg Ser Ala Phe Thr Thr Ser Asp Val Val Arg Met His
    845                 850                 855

3001
GTC GGT GAT GGC AAA CTG CCG TGC CGC TCC AAC ACC TTC CTC AAC ATT
Val Gly Asp Gly Lys Leu Pro Cys Arg Ser Asn Thr Phe Leu Asn Ile
860             865                 870                     875

3049
TTC CGG AGA AAG AAG CCC GGG GCA GGG AAT GCC AAT TCT AAC GGC AAG
Phe Arg Arg Lys Lys Pro Gly Ala Gly Asn Ala Asn Ser Asn Gly Lys
                880                 885                 890

3097
TCT GTG TCA TGG TCT GAA CCA GGT GGA AGA CAG GCG CCC AAG GGA CAG
Ser Val Ser Trp Ser Glu Pro Gly Gly Arg Gln Ala Pro Lys Gly Gln
            895                 900                 905

3145
CAC GTG TGG CAG CGC CTC TCT GTG CAC GTG AAG ACC AAC GAG ACG GCC
His Val Trp Gln Arg Leu Ser Val His Val Lys Thr Asn Glu Thr Ala
        910                 915                 920

3193
TGT AAC CAA ACA GCC GTA ATC AAA CCC CTC ACT AAA AGT TAC CAA GGC
Cys Asn Gln Thr Ala Val Ile Lys Pro Leu Thr Lys Ser Tyr Gln Gly
    925                 930                 935

3241
TCT GGC AAG AGC CTG ACC TTT TCA GAT GCC AGC ACC AAG ACC CTT TAC
Ser Gly Lys Ser Leu Thr Phe Ser Asp Ala Ser Thr Lys Thr Leu Tyr
940             945                 950                     955

3289
AAT GTG GAA GAA GAG GAC AAT ACC CCT TCT GCT CAC TTC AGC CCT CCC
Asn Val Glu Glu Glu Asp Asn Thr Pro Ser Ala His Phe Ser Pro Pro
                960                 965                 970

3337
AGC AGC CCT TCT ATG GTG GTG CAC CGA CGC GGG CCA CCC GTG GCC ACC
Ser Ser Pro Ser Met Val Val His Arg Arg Gly Pro Pro Val Ala Thr
            975                 980                 985

3385
ACA CCA CCT CTG CCA CCC CAT CTG ACC GCA GAA GAG ACC CCC CTG TTC
Thr Pro Pro Leu Pro Pro His Leu Thr Ala Glu Glu Thr Pro Leu Phe
        990                 995                 1000
```

FIG. 5F.

```
                                                                    3433
CTG GCT GAT TCC GTC ATC CCC AAG GGC TTG CCT CCT CCT CTC CCG CAG
Leu Ala Asp Ser Val Ile Pro Lys Gly Leu Pro Pro Pro Leu Pro Gln
        1005            1010            1015

3481
CAG CAG CCA CAG CAG CCG CCC CCT CAG CAG CCC CCG CAG CAG CCC AAG
Gln Gln Pro Gln Gln Pro Pro Pro Gln Gln Pro Pro Gln Gln Pro Lys
1020            1025            1030            1035

3529
TCC CTG ATG GAC CAG CTG CAA GGC GTA GTC ACC AAC TTC GGT TCG GGG
Ser Leu Met Asp Gln Leu Gln Gly Val Val Thr Asn Phe Gly Ser Gly
                1040            1045            1050

3577
ATT CCA GAT TTC CAT GCG GTG CTG GCA GGC CCG GGG ACA CCA GGA AAC
Ile Pro Asp Phe His Ala Val Leu Ala Gly Pro Gly Thr Pro Gly Asn
            1055            1060            1065

3625
AGC CTG CGC TCT CTG TAC CCG CCC CCG CCT CCG CCG CAA CAC CTG CAG
Ser Leu Arg Ser Leu Tyr Pro Pro Pro Pro Pro Pro Gln His Leu Gln
        1070            1075            1080

3673
ATG CTG CCC CTG CAC CTG AGC ACC TTC CAG GAG GAG TCC ATC TCC CCT
Met Leu Pro Leu His Leu Ser Thr Phe Gln Glu Glu Ser Ile Ser Pro
        1085            1090            1095

3721
CCT GGG GAG GAC ATC GAT GAT GAC AGT GAG AGA TTC AAG CTC CTG CAG
Pro Gly Glu Asp Ile Asp Asp Asp Ser Glu Arg Phe Lys Leu Leu Gln
1100            1105            1110            1115

3769
GAG TTC GTG TAC GAG CGC GAA GGG AAC ACC GAA GAA GAT GAA TTG GAA
Glu Phe Val Tyr Glu Arg Glu Gly Asn Thr Glu Glu Asp Glu Leu Glu
                1120            1125            1130

3817
GAG GAG GAG GAC CTG CCC ACA GCC AGC AAG CTG ACC CCT GAG GAT TCT
Glu Glu Glu Asp Leu Pro Thr Ala Ser Lys Leu Thr Pro Glu Asp Ser
            1135            1140            1145

3865
CCT GCC CTG ACG CCT CCT TCT CCT TTC CGA GAT TCC GTG GCC TCT GGC
Pro Ala Leu Thr Pro Pro Ser Pro Phe Arg Asp Ser Val Ala Ser Gly
            1150            1155            1160

3913
AGC TCA GTG CCC AGT TCC CCC GTA TCT GAG TCG GTC CTC TGC ACC CCT
Ser Ser Val Pro Ser Ser Pro Val Ser Glu Ser Val Leu Cys Thr Pro
        1165            1170            1175
```

*FIG. 5G.*

```
                                                                                          3961
CCA AAT GTA ACC TAC GCC TCT GTC ATT CTG AGG GAC TAC AAG CAA AGC
Pro Asn Val Thr Tyr Ala Ser Val Ile Leu Arg Asp Tyr Lys Gln Ser
1180            1185                1190                1195

4013
TCT TCC ACC CTG TAGTGTGTGT GTGTGTGTGG GGGCGGGGGG AGTGCGCATG
Ser Ser Thr Leu

4073
GAGAAGCCAG AGATGCCAAG GAGTGTCAAC CCTTCCAGAA ATGTGTAGAA AGCAGGGTGA

4133
GGGATGGGGA TGGAGGACCA CGGTCTGCAG GGAAGAAAAA AAAAATGCTG CGGCTGCCTT

4193
AAAGAAGGAG AGGGACGATG CCAACTGAAC AGTGGTCCTG GCCAGGATTG TGACTCTTGA

4253
ATTATTCAAA AACCTTCTCT AGAAAGAAAG GGAATTATGA CAAAGCACAA TTCCATATGG

4300
TATGTAACTT TTATCGAAAA AAAAAAAAAA AAAAAAAAA AAAAAAA
```

G PROTEIN COUPLED GLUTAMATE RECEPTORS

RELATED APPLICATIONS

This application is a divisional of Ser. No. 08/101,676, filed Aug. 3, 1993 (now abandoned), which is a continuation-in-part of Ser. No. 07/648,481 filed Jan. 30, 1991 (now abandoned), which is a continuation-in-part of Ser. No. 07/626,806, filed Dec. 12, 1990 (now abandoned) which are incorporated herein by reference.

GOVERNMENT SUPPORT

This invention was made with government support under grant number R37 AR-17803 awarded by the National Institutes of Health. The government has certain rights in the invention.

BACKGROUND OF THE INVENTION

The majority of nerve cell connections are chemical synapses. A neurotransmitter is released from the presynaptic terminal, typically in response to the arrival of an action potential in the neuron, and diffuses across the synaptic space to bind to membrane receptor proteins of the postsynaptic terminal. The binding of neurotransmitters to membrane receptors is coupled either to the generation of a permeability change in the postsynaptic cell or to metabolic changes.

Neurotransmitters produce different effects according to the type of receptor to which they bind. In general, those which produce effects that are rapid in onset and brief in duration bind receptors that act as ligand-gated ion channels, where binding almost instantly causes an ion flow across the membrane of the postsynaptic cell. Those neurotransmitters which act more like local chemical mediators bind to receptors that are coupled to intracellular enzymes, thereby producing effects that are slow in onset and more prolonged. These neurotransmitters alter the concentration of intracellular second messengers in the postsynaptic cell.

Four second messenger systems have been linked to neurotransmitter or hormone receptors and have been studied for their roles in the control of neuronal excitability. They are the adenylate cyclase/cyclic AMP-dependent protein kinase system, guanylate cyclase and cGMP-dependent protein kinase, the inositol trisphosphate/diacyl glycerol-protein kinase C system, and systems which are activated by calcium ions, such as the calcium/calmodulin-dependent protein kinase system. Thus, binding of a transmitter to a receptor may activate, for example, adenylate cyclase, thereby increasing the intracellular concentration of cAMP, which in turn activates protein kinases that phosphorylate specific proteins in the cells, such as those which form ion channels and thus alter the cells' electrical behavior. As with the ligand-gated ion channel transmitters, the effects can be either excitatory or inhibitory, and may affect the cell at many levels, including the pattern of gene expression. It is also believed that these chemical synapses, associated with second-messenger systems, may be involved in long-term changes that comprise the cellular basis of learning and memory.

The ligand-activated membrane receptors do not activate the second messenger systems directly, however, but via a membrane-bound protein, the GTP-binding protein (G protein), which binds GTP on the cytoplasmic surface of the cell membrane and thereby acts to couple adenylate cyclase to the membrane receptor. Neurotransmitter binding to the membrane receptor is believed to alter the conformation of the receptor protein to enable it to activate the G protein in the lipid bilayer, which then binds GTP at the cytoplasmic surface and produces a further change in the G protein to allow it to activate, e.g., an adenylate cyclase molecule to synthesize cAMP. When a ligand binds a receptor, an enzymatic cascade results as each receptor activates several molecules of G protein, which in turn activate more molecules of adenylate cyclase which convert an even larger number of ATPs to cAMP molecules, producing a substantial amplification from the initial event.

Glutamate, aspartate and their endogenous derivatives are believed to be the predominant excitatory neurotransmitters in the vertebrate central nervous system. (Krinjrvic, *Phys. Rev.* 54:418–540, 1974). Recently, glutamate has been described as playing a major, widespread role in the control of neuroendocrine neurons, possibly controlling not only the neuroendocrine system but other hypothalamic regions as well. Four major subclasses of glutamate receptors have been described but their characterization has until recently been limited to pharmacological and electrophysiological functional analyses. See generally, Hollman et al., *Nature* 342:643–648 (1989) and Sommer et al., *Science* 249:1580–1585 (1990). Three of the receptors, the quisqualate (QA/AMPA), kainate (KA), and N-methyl-D-aspartate (NMDA) receptors, are believed to be directly coupled to cation-specific ion channels and thus are classified as ligand-gated ionotropic receptors. The fourth glutamate receptor binds some of the agonists of the ionotropic receptors (quisqualate and glutamate, but not AMPA) but has no shared antagonists, and is coupled to G protein. Thus, this receptor, referred to as the G protein-coupled glutamate receptor, or $Glu_GR$, is pharmacologically and functionally distinct from the other major glutamate receptors. This receptor has also been termed the metabotropic receptor.

Agonist binding to $Glu_GR$ has been shown to result in the activation of a number of second messenger systems, depending on the system studied. One of the best characterized is the quisqualate activation of phospholipase C through a G protein coupled interaction that leads to the stimulation of inositol phospholipid metabolism. This activity has been studied in systems that measure the accumulation of radiolabeled inositol monophosphate in response to stimulation by glutamate. The systems typically use brain slices from regions such as the hippocampus, striatum, cerebral cortex and hypothalamus (Nicoletti, et al., *Proc. Natl. Acad. Sci. USA* 83:1931–1935 (1986), and Nicoletti, et al., *J. Neurochem.* 46:40–46 (1986)) neuronal cultures derived from embryonic mouse and rat cerebellum, corpus striatum and cerebral cortex (Nicoletti et al., *J. Neurosci.* 6:1905–1911 (1986), Sladeczek et al., *Nature* 317:717–719 (1985), Dumuis, et al., *Nature* 347:182–184 (1990), and Drejer et al., *J. Neurosci.* 7:2910–2916 (1987)) and rat brain synaptosomes (Recasens et al., *Eur. J. Pharm.* 141: 87–93 (1987), and Recasens et al., *Neurochem. Int.* 13:463–467 (1988)). A major disadvantage of each of these model systems is the difficulty in analyzing the pharmacological and functional activities of $Glu_GR$ in an environment where other glutamate receptors and G protein-coupled receptors such as muscarinic and serotonin receptors are also present.

The Xenopus oocyte system has been used to identify $Glu_GR$ as a member of the family of G protein-coupled receptors. An endogenous inositol triphosphate second messenger-mediated pathway in the oocyte allows the detection of $Glu_GR$ after injection of total rat brain mRNA, in that the oocyte responds to ligand via the oocyte G protein-coupled PLC-mediated activation of a chloride channel that can be detected as a delayed, oscillatory current by voltage-clamp recording (Houamed et al., *Nature* 310:318–321 (1984); Gunderson et al., *Proc. Royal Soc.* B221:127–143 (1984); Dascal et al., *Mol. Brain Res.* 1:301–309 (1986); Verdoorn et al., *Science* 238:1114–1116 (1987); Sugiyama et al., *Nature* 325:531–533 (1987); Hirono et al., *Neuros. Res.* 6:106–114 (1988); Verdoorn and Dingledine, *Mol. Pharmacol.* 34:298–307 (1988); and Sugiyama et al., *Neuron* 3:129–132 (1989)). Injection of region-specific brain mRNA and of size fractionated mRNA have suggested that $Glu_GR$ may be a large mRNA (6–7 kb) and that it is enriched in the cerebellum (Fong et al., *Synapse* 2:657–665 (1988) and Horikoshi et al., *Neurosci. Lett.* 105:340–343 (1989)).

There remains considerable need in the art for isolated and purified $Glu_GR$, as well as systems capable of expressing $Glu_GR$ separate from other neurotransmitter receptors. Further, it would be desirable to specifically identify the presence of $Glu_GR$ in cells and tissues, thereby avoiding the time-consuming, complex and nonspecific functional electrophysiological and pharmacological assays. It would also be desirable to screen and develop new agonists and/or antagonists specific for $Glu_GR$, but to date this has not been practical. Quite surprisingly, the present invention fulfills these and other related needs.

SUMMARY OF THE INVENTION

The present invention provides isolated and substantially pure preparations of mammalian G protein-coupled glutamate receptors and fragments thereof. In preferred embodiments the receptors are coupled to a G protein in vertebrate cells, bind glutamate and quisqualate and thereby activate phospholipase C, and are capable of stimulating inositol phospholipid metabolism. Having provided such receptors in isolated and purified form, the invention also provides antibodies to the receptors, in the form of antisera and/or monoclonal antibodies.

In another aspect the invention provides the ability to produce the mammalian G protein-coupled glutamate receptors and polypeptides or fragments thereof by recombinant means, preferably in cultured eukaryotic cells. The expressed receptors or fragments may or may not have the biological activity of native receptors, and may or may not be coupled to a G protein in the cell used for expression. Accordingly, isolated and purified polynucleotides are described which code for the receptor and fragments thereof, where the polynucleotides may be in the form of DNA, such as cDNA or RNA. Based on these sequences probes may be used to hybridize and identify these and related genes which encode mammalian G protein-coupled glutamate receptors. The probes may be full length cDNA or as small as from 14 to 25 nucleotide, more often though from about 40 to about 50 or more nucleotides.

In related embodiments the invention concerns DNA constructs which comprise a transcriptional promoter, a DNA sequence which encodes the receptor or fragment, and a transcriptional terminator, each operably linked for expression of the receptor. For expression the construct may also contain at least one signal sequence. The constructs are preferably used to transform or transfect eukaryotic cells, more preferably mammalian cells which do not express endogenous G protein-coupled glutamate receptors. When bound by an appropriate ligand such as glutamate or quisqualate, the receptor may activate phospholipase C in the host cell via coupling to G protein. Further, for large scale production the expressed receptor may also be isolated from the cells by, for example, immunoaffinity purification.

Cells which express the G protein-coupled glutamate receptors may also be used to identify compounds which can alter the receptor-mediated metabolism of a eukaryotic cell. Compounds may be screened for binding to the receptor, and/or for effecting a change in receptor-mediated metabolism in the host cell. Agonists and/or antagonists of the G protein-coupled glutamate receptors may also be screened in cell-free systems using purified receptors or binding fragments thereof for the effect on ligand-receptor interaction, or using reconstituted systems such micelles which also provide the ability to assess metabolic changes.

In yet other embodiments the invention relates to methods for diagnosis, where the presence of a mammalian G protein-coupled glutamate receptor in a biological sample may be determined. For example, a monospecific antibody which specifically binds the receptor is incubated with the sample under conditions conducive to immune complex formation, which complexes are then detected, typically by means of a label such as an enzyme, fluorophore, radionuclide, chemiluminiscer, particle, or a second labeled antibody. Thus, means are provided for immunohistochemical staining of tissues, including brain tissues, for the subject receptors.

BRIEF DESCRIPTION OF THE DRAWINGS

FIG. 1 illustrates the construction of plasmid pVEGT, where

FIG. 2 illustrates representative responses from voltage-clamp assays of oocytes injected with RNA from positive pools.

FIG. 5 illustrates the DNA sequence and deduced amino acid sequence of clone 45-A (corresponding to Sequence ID Nos. 1 and 2). Numbers below the line refer to amino acid sequence, numbers to the right of the line refer to nucleotide number. Putative transmembrane domains have been overlined, and putative N-linked glycosylation sites are indicated by closed circles.

Figure 1A:
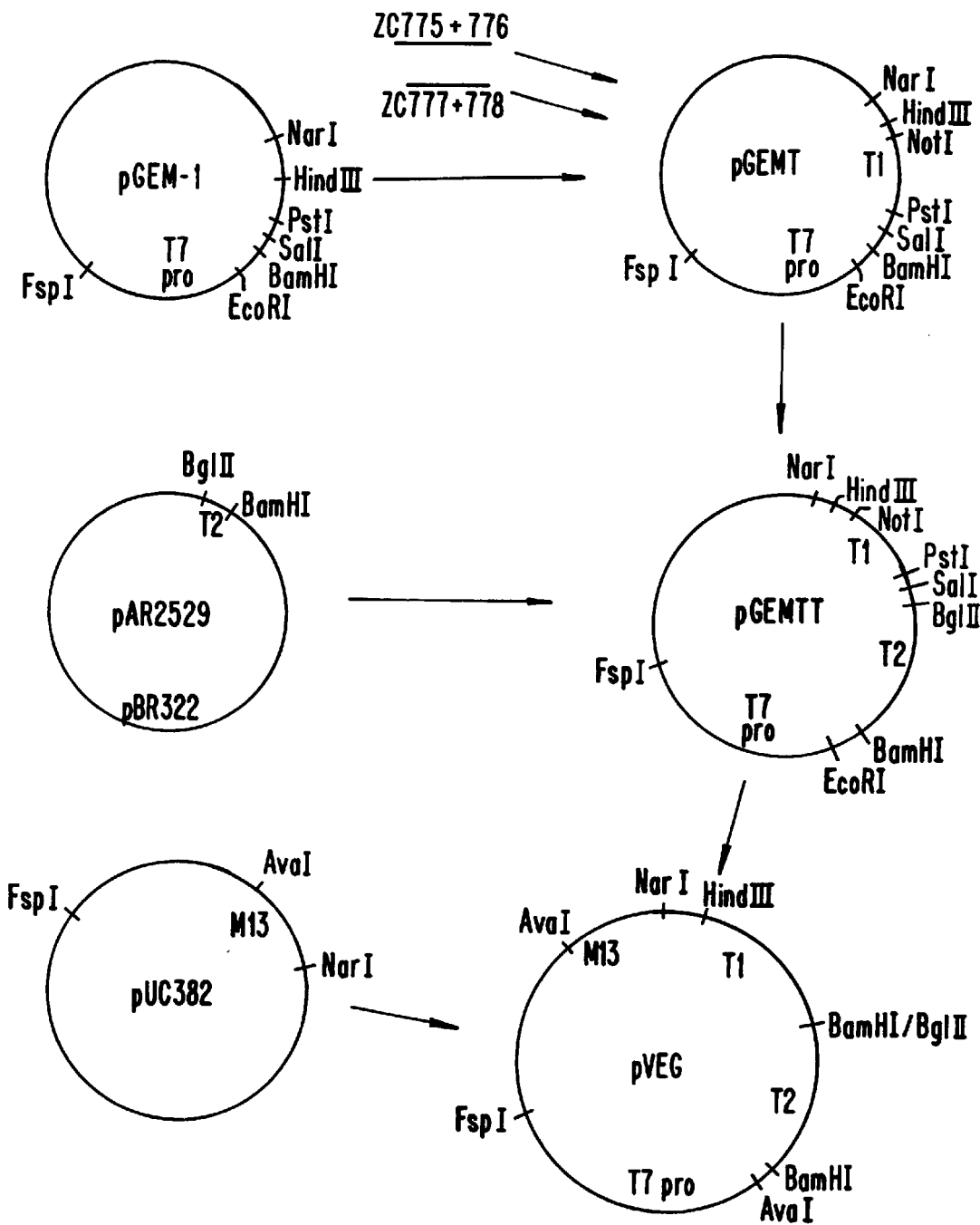
FIG. 1A shows the construction of pVEG.

DESCRIPTION OF THE PREFERRED EMBODIMENTS $Glu_GR$ is a G protein coupled membrane receptor for the neurotransmitter glutamate. As glutamate has been described as having a major role in the control of neurons, particularly neuroendocrine neurons, $Glu_GR$ may play a critical role in effectuating such control. Consequently, the development of agonists and antagonists of the $Glu_GR$-ligand interaction and $Glu_GR$-mediated metabolism is of great interest.

The present invention presents the means to identify agonists and antagonists of the $Glu_GR$-ligand interaction by providing isolated $Glu_GR$. The term "$Glu_GR$" refers to any protein either derived from a naturally occurring $Glu_GR$, or which shares significant structural and functional characteristics peculiar to a naturally occurring $Glu_GR$. Such a receptor may result when regions of a naturally occurring receptor are deleted or replaced in such a manner as to yield a protein having a similar function. Homologous sequences, allelic variations, and natural mutants; induced point, deletion, and insertion mutants; alternatively expressed variants; proteins encoded by DNA which hybridize under high or low stringency conditions to nucleic acids which encode naturally occurring $Glu_GR$-encoding nucleic acids; proteins retrieved from naturally occurring materials; and closely related proteins retrieved by antisera directed against $Glu_GR$ proteins are also included.

By $Glu_GR$ "ligand" is meant a molecule capable of being bound by the ligand-binding domain of $Glu_GR$, a $Glu_GR$ analog, or chimeric $Glu_GR$ as generally described in U.S. Pat. No. 4,859,609, incorporated by reference herein. The molecule may be chemically synthesized or may occur in nature. Ligands may be grouped into agonists and antagonists. Agonists are those molecules whose binding to a receptor induces the response pathway within a cell. Antagonists are those molecules whose binding to a receptor blocks the response pathway within a cell.

By "isolated" $Glu_GR$ is meant to refer to $Glu_GR$ which is in other than its native environment such as a neuron, including, for example, substantially pure $Glu_GR$ as defined hereinbelow. More generally, isolated is meant to include $Glu_GR$ as a heterologous component of a cell or other system. For example, $Glu_GR$ may be expressed by a cell transfected with a DNA construct which encodes $Glu_GR$, separated from the cell and added to micelles which contain other selected receptors. In another example described below, $Glu_GR$ is expressed by a cell which has been co-transfected with a gene encoding muscarinic receptor. Thus, in this context, the environment of isolated $Glu_GR$ is not as it occurs in its native state, particularly when it is present in a system as an exogenous component.

The invention provides cloned $Glu_GR$ coding sequences which are capable of expressing the $Glu_GR$ protein. Complementary DNA encoding $Glu_GR$ may be obtained by constructing a cDNA library from mRNA from, for example, brain tissue. The library may be screened by transcribing the library and injecting the resulting mRNA into oocytes and detecting, by functional assays, those oocytes which express the $Glu_GR$. Alternatively, the clones may be screened with a complementary labeled oligonucleotide probe.

The present invention relates to successfully isolating a cDNA encoding a $Glu_GR$. Functional cloning of $Glu_GR$ was accomplished by substantial modifications and improvements to a number of cDNA cloning and molecular biology techniques. Initially, an enriched source of $Glu_GR$ mRNA prepared by sucrose gradient centrifugation of >4 kb length rat cerebellum poly (A)+ mRNA was used as template for cDNA synthesis. Further, a cDNA cloning vector that was employed included a poly (A) tail, thereby increasing by 40-fold the translational efficiency of the transcription product of the cDNA insert and a polylinker site to allow the directional cloning of the cDNA into the vector between the promoter and the poly (A) tail. Vector construction for directional cloning is described in co-pending U.S. Ser. No. 07/320,191, incorporated herein by reference. The cDNA cloning vector also was used with two transcriptional terminators, in tandem, following the poly (A) sequences, efficiently generating a unit length transcript product without non-coding plasmid or viral sequences, and without requiring a restriction endonuclease to linearize the DNA template (a standard practice that will often prevent functional cloning strategies from working due to the presence of the endonuclease site within the coding region of the cDNA). The cDNA synthesis strategy maximized insert size and recreation of the 5' end of the cDNA's, without introduction of homopolymer tails. cDNA inserts were size-selected to be greater than 4 kb in length before insertion into the vector. A library of $10^6$ cDNA inserts in pools of 100,000 were replica plated to cut down on the number of amplification steps in the fractionation of sequentially smaller pools. Moreover, m1 muscarinic cDNA (another G protein-coupled receptor coupled to phosphoinositol metabolism) template was included in transcription reactions of the subfractionated pools so that before injection the in vitro transcripts from each pool could be assayed by Northern analysis to assess relative quantity and quality of the mRNA, and by voltage-clamp of oocytes as an internal positive control for each oocyte not responding to quisqualate or glutamate. The inclusion of a dilution of SEAP-VEGT' (a secreted form of alkaline phosphatase) template in transcriptions was also employed so that oocytes selected for voltage-clamp analysis were those synthesizing higher levels of the co-injected $Glu_GR$ mRNA. And further, low noise electrical recording techniques were used to monitor the small signals initially generated from rare transcripts.

With the $Glu_GR$ and cDNA clones thereof provided herein, nucleotide and amino acid sequences may be determined by conventional means, such as by dideoxy sequencing. See generally, Sambrook et al., *Molecular Cloning, A Laboratory Manual,* 2d ed., Cold Spring Harbor Laboratory Press, Cold Spring Harbor, N.Y., 1989, incorporated by reference herein. Genomic or cDNA sequences encoding $Glu_GR$ and homologous receptors of this family may be obtained from libraries prepared from other mammalian species according to well known procedures. For instance, using oligonucleotide probes from rodent $Glu_GR$, such as whole length cDNA or shorter probes of at least about fourteen nucleotides to twenty-five or more nucleotides in length; often as many as 40 to 50 nucleotides, DNA sequences encoding $Glu_GR$ of other mammalian species, such as lagomorph, avian, bovine, porcine, murine, etc. may be obtained. If partial clones are obtained, it is necessary to join them in proper reading frame to produce a full length clone, using such techniques as endonuclease cleavage, ligation and loopout mutagenesis.

A DNA sequence encoding $Glu_GR$ is inserted into a suitable expression vector, which in turn is used to transfect eukaryotic cells. Expression vectors for use in carrying out the present invention will comprise a promoter capable of directing the transcription of a cloned DNA and a transcriptional terminator.

To direct proteins of the present invention for transport to the plasma membrane, at least one signal sequence is operably linked to the DNA sequence of interest. The signal sequence may be derived from the $Glu_GR$ coding sequence, from other signal sequences described in the art, or synthesized de novo.

Host cells for use in practicing the present invention include mammalian, avian, plant, insect and fungal cells, but preferably mammalian cells. Fungal cells, including species of yeast (e.g., Saccharomyces spp., particularly *S. cerevisiae,* Schizosaccharomyces spp.) or filamentous fungi (e.g., Aspergillus spp., Neurospora spp.) may be used as host cells within the present invention. Suitable yeast vectors for use in the present invention include YRp7 (Struhl et al., *Proc. Natl. Acad, Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs,

*Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8: 17, 1979), HIS3 (Struhl et al., ibid.) or POT1 (Kawasaki et al., ibid.). Another suitable selectable marker is the CAT gene, which confers chloramphenicol resistance on yeast cells.

Additional vectors, promoters and terminators for use in expressing the receptor of the invention in yeast are well known in the art and are reviewed by, for example, Emr, *Meth. Enzymol.* 185:231–279, (1990), incorporated herein by reference. The receptors of the invention may be expressed in Aspergillus spp. (McKnight and Upshall, described in U.S. Pat. No. 4,935,349, which is incorporated herein by reference). Useful promoters include those derived from *Aspergillus nidulans* glycolytic genes, such as the ADH3 promoter (McKnight et al., *EMBO J.* 4:2093–2099, 1985) and the tpiA promoter. An example of a suitable terminator is the ADH3 terminator (McKnight et al., ibid.). Techniques for transforming fungi are well known in the literature, and have been described, for instance by Beggs (ibid.), Hinnen et al. (*Proc. Natl. Acad. Sci. USA* 75:1929–1933, 1978), Yelton et al. (*Proc. Natl. Acad. Sci. USA* 81:1740– 1747, 1984), and Russell (*Nature* 301:167–169, 1983) each of which are incorporated herein by reference.

A variety of higher eukaryotic cells may serve as host cells for expression of the $Glu_GR$, although not all cell lines will be capable of functional coupling of the receptor to the cell's second messenger systems. Cultured mammalian cells, such as BHK, CHO, Y1 (Shapiro et al., *TIPS Suppl.* 43–46 (1989)), NG108-15 (Dawson et al., *Neuroscience Approached Through Cell Culture*, Vol. 2, pages 89–114 (1989)), N1E-115 (Liles et al., *J. Biol. Chem.* 261:5307–5313 (1986)), PC 12 and COS-1 (ATCC CRL 1650) are preferred. Preferred BHK cell lines are the tk⁻ts13 BHK cell line (Waechter and Baserga, *Proc. Natl. Acad. Sci. USA* 79:1106–1110 (1982)) and the BHK 570 cell line (deposited with the American Type Culture Collection, 12301 Parklawn Dr., Rockville, Md. under accession number CRL 10314). A tk⁻BHK cell line is available from the ATCC under accession number CRL 1632.

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41: 521–530, 1985) and the SV40 promoter (Subramani et al., *Mol. Cell. Biol.* 1: 854–864, 1981). Cellular promoters include the mouse metallothionein-1 promoter (Palmiter et al., U.S. Pat. No. 4,579,821), a mouse $V_\kappa$ promoter (Bergman et al., *Proc. Natl. Acad. Sci. USA* 81: 7041–7045, 1983; Grant et al., Nuc. Acids Res. 15: 5496, 1987) and a mouse $V_H$ promoter (Loh et al., *Cell* 33: 85–93, 1983). A particularly preferred promoter is the major late promoter from Adenovirus 2 (Kaufman and Sharp, *Mol. Cell. Biol.* 2: 1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes.

Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9: 3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse $\mu$ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973.) Other techniques for introducing cloned DNA sequences into mammalian cells, such as electroporation (Neumann et al., *EMBO J.* 1: 841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. Transfected cells may also be selected in the presence of antagonist to inhibit the activity of the receptor. Suitable antagonists in this context include D, L, 2-amino-3-phosphonopropionate. For cells that have been transfected with an amplifiable selectable marker the drug concentration may be increased in a stepwise manner to select for increased copy number of the cloned sequences, thereby increasing expression levels.

Promoters, terminators and methods suitable for introducing expression vectors encoding recombinant $Glu_GR$ into plant, avian and insect cells are known in the art. The use of baculoviruses, for example, as vectors for expressing heterologous DNA sequences in insect cells has been reviewed by Atkinson et al. (*Pestic. Sci.* 28: 215–224,1990). The use of *Agrobacterium rhizogenes* as vectors for expressing genes in plant cells has been reviewed by Sinkar et al. (*J. Biosci. (Banglaore)* 11: 47–58, 1987).

Host cells containing DNA constructs of the present invention are then cultured to produce recombinant $Glu_GR$. The cells are cultured according to accepted methods in a culture medium containing nutrients required for growth of mammalian or other host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

The $Glu_GR$ produced according to the present invention may be purified from the recombinant expression systems or other sources using purification protocols that employ techniques generally available to those skilled in the art. The most convenient sources for obtaining large quantities of $Glu_GR$ are cells which express the recombinant receptor. However, other sources, such as tissues, particularly brain tissues of the cerebellum which contain $Glu_GR$ may also be employed.

Purification may be achieved by conventional chemical purification means, such as liquid chromatography, lectin affinity chromatography, gradient centrifugation, and gel electrophoresis, among others. Methods of protein purification are known in the art (see generally, Scopes, R., *Protein Purification, Springer-Verlag, N.Y.* (1982), which is incorporated herein by reference) and may be applied to the purification of the $Glu_GR$ and particularly the recombinantly produced $Glu_GR$ described herein. In a preferred embodiment immunoaffinity chromatography is employed using antibodies directed against $Glu_GR$ as herein described. In another method of purification, the recombinant gene encoding $Glu_GR$ or portions thereof can be modified at the amino terminus, just behind a signal peptide, with a sequence coding for a small hydrophilic peptide, such as described in U.S. Pat. Nos. 4,703,004 and 4,782,137, incorporated herein by reference. Specific antibodies for the peptide facilitate rapid purification of $Glu_GR$, and the short peptide can then be removed with enterokinase.

Thus, as discussed above, the present invention provides $Glu_GR$ isolated from its natural cellular environment, substantially free of other G protein coupled glutamate receptors. Purified $Glu_GR$ is also provided. Substantially pure $Glu_GR$ of at least about 50% is preferred, at least about 70–80% more preferred, and 95–99% or more homogeneity most preferred, particularly for pharmaceutical uses. Once purified, partially or to homogeneity, as desired, the recombinant $Glu_GR$ or native $Glu_GR$ may then be used to generate antibodies, in assay procedures, etc.

In another aspect, the invention concerns polypeptides and fragments of $Glu_GR$. Polypeptides and fragments of $Glu_GR$ may be isolated from recombinant expression systems or may be synthesized by the solid phase method of Merrifield, *Fed. Proc.* 21:412 (1962), Merrifield, *J. Am. Chem. Soc.* 85:2149 (1963), or Barany and Merrifield, in *The Peptides*, vol. 2, pp. 1–284 (1979) Academic Press, N.Y., each of which are incorporated herein by reference, or by use of an automated peptide synthesizer. By "polypeptides" is meant a sequence of at least about 3 amino acids, typically 6 or more, up to 100–200 amino acids or more, including entire proteins. For example, the portion(s) of $Glu_GR$ protein which binds ligand may be identified by a variety of methods, such as by treating purified receptor with a protease or a chemical agent to fragment it and determine which fragment is able to bind to labeled glutamate in a ligand blot. Polypeptides may then be synthesized and used as antigen, to inhibit ligand-$Glu_GR$ interaction, etc. It should be understood that as used herein, reference to $Glu_GR$ is meant to include the protein, polypeptides, and fragments thereof unless the context indicates otherwise.

In another aspect, the invention provides means for regulating the $Glu_GR$-ligand interaction, and thus treating, therapeutically and/or prophylactically, a disorder which can be linked directly or indirectly to $Glu_GR$ or to its ligands, such as glutamate and other endogenous excitatory amino acids. By virtue of having the receptor of the invention, agonists or antagonists may be identified which stimulate or inhibit the interaction of ligand with $Glu_GR$. With either agonists or antagonists the metabolism and reactivity of cells which express the receptor are controlled, thereby providing a means to abate or in some instances prevent the disease of interest.

Thus, the invention provides screening procedures for identifying agonists or antagonists of events mediated by the ligand-$Glu_GR$ interaction. Such screening assays may employ a wide variety of formats, depending to some extent on which aspect of the ligand/receptor/G protein interaction is targeted. For example, such assays may be designed to identify compounds which bind to the receptor and thereby block or inhibit interaction of the receptor with the ligand. Other assays can be designed to identify compounds which can substitute for ligand and therefore stimulate $Glu_GR$-mediated intracellular pathways. Yet other assays can be used to identify compounds which inhibit or facilitate the association of $Glu_GR$ to G protein and thereby mediate the cellular response to $Glu_GR$ ligand.

In one functional screening assay, the initiation of fertilization activation events are monitored in eggs which have been injected with, e.g., mRNA which codes for $Glu_GR$ and subsequently exposed to selected compounds which are being screened, in conjunction with or apart from an appropriate ligand. See generally, Kline et al., *Science* 241:464–467 (1988), incorporated herein by reference.

Another screening assay is based on the use of mammalian cell lines which express $Glu_GR$ functionally coupled to a mammalian G protein. In this assay, compounds are screened for their relative affinity as receptor agonists or antagonists by comparing the relative receptor occupancy to the extent of ligand induced stimulation or inhibition of second messenger metabolism. For example, activation of phospholipase C leads to increased inositol monophosphate metabolism. Means for measuring inositol monophosphate metabolism are generally described in Subers and Nathanson, *J. Mol. Cell. Cardiol,* 20:131–140 (1988), incorporated herein by reference.

The screening procedure can be used to identify reagents such as antibodies which specifically bind to the receptor and substantially affect its interaction with ligand, for example. The antibodies may be monoclonal or polyclonal, in the form of antiserum or monospecific antibodies, such as purified antiserum or monoclonal antibodies or mixtures thereof. For administration to humans, e.g., as a component of a composition for in vivo diagnosis or imaging, the antibodies are preferably substantially human to minimize immunogenicity and are in substantially pure form. By substantially human is meant generally containing at least about 70% human antibody sequence, preferably at least about 80% human, and most preferably at least about 90–95% or more of a human antibody sequence to minimize immunogenicity in humans.

Antibodies which bind $Glu_GR$ may be produced by a variety of means. The production of non-human antisera or monoclonal antibodies, e.g., murine, lagomorpha, equine, etc. is well known and may be accomplished by, for example, immunizing the animal with the receptor molecule or a preparation containing a desired portion of the receptor molecule, such as that domain or domains which contributes to ligand binding. For the production of monoclonal antibodies, antibody producing cells obtained from immunized animals are immortalized and screened, or screened first for the production of antibody which binds to the receptor protein and then immortalized. As the generation of human monoclonal antibodies to human $Glu_GR$ antigen may be difficult with conventional techniques, it may be desirable to transfer antigen binding regions of the non-human antibodies, e.g. the $F(ab')_2$ or hypervariable regions, to human constant regions (Fc) or framework regions by recombinant DNA techniques to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences which code for a human monoclonal antibody or portions thereof that specifically bind to the human receptor protein by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

In other embodiments, the invention provides screening assays conducted in vitro with cells which express the receptor. For example, the DNA which encodes the receptor or selected portions thereof may be transfected into an established cell line, e.g., a mammalian cell line such as BHK or CHO, using procedures known in the art (see, e.g., Sambrook et al., *Molecular Cloning, A Laboratory Manual*, 2d ed., Cold Spring Harbor Laboratory Press, Cold Spring Harbor, N.Y., 1989, is in is incorporated herein by reference). The receptor is then expressed by the cultured cells, and selected agents are screened for the desired effect on the cell, separately or in conjunction with an appropriate ligand such as glutamate or quisqualate. Means for amplifying nucleic acid sequences which may be employed to amplify sequences encoding the receptor or portions thereof are described in U.S. Pat. Nos. 4,683,195 and 4,683,202, incorporated herein by reference.

In yet another aspect, the screening assays provided by the invention relate to transgenic mammals whose germ cells and somatic cells contain a nucleotide sequence encoding $Glu_GR$ protein or a selected portion of the receptor which, e.g., binds ligand, GTP binding protein, or the like. There are several means by which a sequence encoding, for example, the human $Glu_GR$ may be introduced into a non-human mammalian embryo, some of which are described in, e.g., U.S. Pat. No. 4,736,866, Jaenisch, *Science* 240–1468–1474 (1988) and Westphal et al., *Annu. Rev. Cell Biol.* 5:181–196 (1989), which are incorporated herein by reference. The animal's cells then express the receptor and thus may be used as a convenient model for testing or screening selected agonists or antagonists.

In another aspect the invention concerns diagnostic methods and compositions. By means of having the $Glu_GR$ molecule and antibodies thereto, a variety of diagnostic assays are provided. For example, with antibodies, including monoclonal antibodies, to $Glu_GR$, the presence and/or concentration of receptor in selected cells or tissues in an individual or culture of interest may be determined. These assays can be used in the diagnosis and/or treatment of diseases such as, for example, cerebral ischemia, Parkinsons, senile dementia and other cognitive disorders, Huntington's chorea, amyotrophic lateral sclerosis, emesis, migraine, and others.

Numerous types of immunoassays are available and are known to those skilled in the art, e.g., competitive assays, sandwich assays, and the like, as generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, New York (1988), each incorporated by reference herein. In one assay format $Glu_GR$ is identified and/or quantified by using labeled antibodies, preferably monoclonal antibodies which are reacted with brain tissues, e.g., cortex, striatum, hippocampus, cerebellum, and determining the specific binding thereto, the assay typically being performed under conditions conducive to immune complex formation. Unlabeled primary antibody can be used in combination with labels that are reactive with primary antibody to detect the receptor. For example, the primary antibody may be detected indirectly by a labeled secondary antibody made to specifically detect the primary antibody. Alternatively, the anti-$Glu_GR$ antibody can be directly labeled. A wide variety of labels may be employed, such as radionuclides, particles (e.g., gold, ferritin, magnetic particles, red blood cells), fluorophores, chemiluminescers, enzymes, enzyme substrates, enzyme cofactors, enzyme inhibitors, ligands (particularly haptens), etc.

The $Glu_GR$ DNA may be directly detected in cells with a labeled $Glu_GR$ DNA or synthetic oligonucleotide probe in a hybridization procedure similar to the Southern or dot blot. Also, the polymerase chain reaction (Saiki et al., *Science* 239:487 (1988), and U.S. Pat. No. 4,683,195) may be used to amplify DNA sequences, which are subsequently detected by their characteristic size on agarose gels, Southern blot of these gels using $Glu_GR$ DNA or a oligonucleotide probe, or a dot blot using similar probes. The probes may comprise from about 14 nucleotides to about 25 or more nucleotides, preferably, 40 to 60 nucleotides, and in some instances a substantial portion or even the entire cDNA of $Glu_GR$ may be used. The probes are labeled with a with a detectable signal, such as an enzyme, biotin, a radionuclide, fluorophore, chemiluminescer, paramagnetic particle, etc.

Kits can also be supplied for use with the receptor of the subject invention in the detection of the presence of the receptor or antibodies thereto, as might be desired in the case of autoimmune disease. Thus, antibodies to $Glu_GR$, preferably monospecific antibodies such as monoclonal antibodies, or compositions of the receptor may be provided, usually in lyophilized form in a container, either segregated or in conjunction with additional reagents, such as anti-antibodies, labels, gene probes, polymerase chain reaction primers and polymerase, and the like.

The following examples are offered by way of illustration, not by limitation.

EXAMPLE I

Preparation of $Glu_gR$ enriched mRNA

Total RNA was prepared from the cerebellum of rats using guanidine isothiocyanate (Chirgwin et al. *Biochemistry*

18:52–94 (1979)) and CsCl centrifugation. Poly (A)+ RNA was isolated using oligo d(T) cellulose chromatography. After 2 rounds of chromatography on oligo d(T) cellulose the RNA (800 µg) was divided into two aliquots and layered over 10–40% linear sucrose gradients in tubes for an SW 28 rotor. The gradients were centrifuged for 28 hours at 25,000 rpm to pellet RNA greater than 4 kb in size. The enriched RNA was injected into frog oocytes and assayed for the presence of the $Glu_G R$.

Injection of oocytes and voltage-clamp assay of $Glu_G R$ activity

Oocytes were prepared from ovarian lobes that were surgically removed from anesthetized Xenopus females. The ovarian lobes were washed, pulled apart into small clumps and dissociated by treatment with collagenase for 2–3 hours at 20° C. with constant, gentle agitation. The dissociation and defolicularization of the oocytes is completed manually after removal of the collagenase. Oocytes that were judged healthy and greater than 1 mm in diameter were transferred to a 50 mm sterile tissue culture dish and incubated in sterile, antibiotic-supplemented Barth's medium (88 mM NaCl, 1 mM KCl, 0.82 mM $MgSO_4$, 0.33 mM $Ca(NO_3)_2$, 0.41 mM $CaCl_2$, 2.4 mM $NaHCO_3$, 10 mM HEPES, pH 7.4, 0.1 mg/ml gentamicin, 0.01 mg/ml penicillin, 0.01 mg/ml streptomycin, 0.5 mM theophylline, and 2.5 mM Na pyruvate) at 19° C.

Injection pipettes were pulled from hard glass tubing (Drummond) on a modified 700C Kopf vertical puller. The tip was broken and bevelled using a List Medical microforge. Tip diameters of the pipettes ranged from 20–30 mM. Injection pipettes were made RNase free by heating to 285° C. overnight.

Following overnight incubation, healthy oocytes were selected for injection. RNA, which was stored at −70° C. in DEPC-treated water, was thawed and centrifuged at 15,000 g for five minutes. Injection was performed using a modified pipetting device (Drummond). After injection, the oocytes were incubated in fresh, sterile Barth's medium which was changed daily, and unhealthy oocytes were removed.

Voltage-clamp assays were carried out on injected oocytes which were each placed in a small chamber of approximately 500 µl in volume and which was continuously perfused with standard frog Ringer's (115 mM NaCl, 2.5 mM KCl, 1.8 mM $CaCl_2$, 10 mM HEPES, pH 7.2) at 1–6 ml/min. The oocyte was impaled with two glass microelectrodes for recording which, when filled with 3M KCl, had a tip resistance of 0.5 to 7.0 megaohms. One of the two electrodes was connected to a differential amplifier via a silver/silver chloride half cell. The bath potential was measured by connecting the other side of the differential amplifier to the bath via a silver/silver chloride pellet and a Ringer/Agar bridge. A low noise, high compliance, voltage-clamp system (NPI) was used to control the membrane potential and to measure membrane current. The oocyte membrane potential was maintained at −60 mV (inside cell negative). One millimolar glutamate (Sigma), 100 µM quisqualate (Sigma), 1 mM carbamylcholine (Sigma), and the other drugs used in this assay were applied by switching the perfusing medium to a medium containing a drug for approximately three minutes, and the membrane current was recorded on a chart recorder (Linear Instruments).

After impaling the oocyte with the two microelectrodes, and imposing the voltage-clamp, the membrane current (the holding current) gradually declines to a steady state over a period of several minutes. When the holding current stabilizes, so that the chart record is horizontal, the drug is applied for one to three minutes. An oocyte is judged to have a positive response if a rapid inward current spike (downward deflection on the chart), followed by slow current oscillations of decreasing magnitude, is observed. Our lower limit of detection depended on the steadiness of the holding current prior to drug application, but was in the range of 5–10 nA.

Construction of pVEGT'

To permit transcription of cloned cDNA without prior endonuclease digestion, bacteriophage T7 transcriptional terminators were added to a cloning vector. Plasmid pVEGT' is described in copending U.S. Ser. No. 07/581,342, which is incorporated by reference herein. The sequence of the putative T7 RNA transcription terminator, which lies between gene 10 and gene 11 of bacteriophage T7, is disclosed by Dunn and Studier (J. Mol. Biol. 166: 477–536 (1983)). As shown in FIG. 5, four synthetic oligonucleotides were designed from this sequence and ligated into the vector pGEM-1 (obtained from Promega Biotec, Madison, Wis.), a plasmid containing a bacterial origin of replication, ampicillin resistance gene, and the T7 promoter adjacent to a multiple cloning site. Terminal phosphates were added to the 5' ends of oligonucleotides ZC776 and ZC777 (Sequence ID Nos. 4 and 5) with T4 polynucleotide kinase and ATP, under standard conditions (Maniatis et al. ibid). (The sequences of these and other oligonucleotides referred to herein are shown in Table 1.) After the incubation, the kinase was heat killed at 65° C. for 10 min. Twenty-five nanograms of oligonucleotide ZC775 (Sequence ID Number 3) and 25 ng of oligonucleotide ZC776 (Sequence ID Number 4) were annealed by incubation at 65° C for 15 minutes, then allowed to cool to room temperature in 500 ml of water. Oligonucleotides ZC777 and ZC778 (Sequence ID Nos. 5 and 6) were similarly annealed. The annealed oligonucleotides were stored at −20° C. until use. The vector pGEM-1 was digested with Pst I and Hind III, and the linearized vector DNA was purified by agarose gel electrophoresis. The synthetic T7 terminator (annealed oligonucleotides ZC775, ZC776, ZC777 and ZC778; Sequence ID Nos. 3, 4, 5 and 6) was then cloned into pGEM-1 . Twenty-five nanograms of vector plus an equal molar amount of each of the annealed oligonucleotides ZC775/ZC776 (Sequence ID Nos. 3 and 4) and ZC777/ZC778 (Sequence ID Nos. 5 and 6) were combined in a 10 µl reaction mix. After an overnight ligation at 14° C., the DNA was transformed into competent E. coli JM83 cells, and the transformed cells were selected for ampicillin resistance. Plasmid DNA was prepared from selected transformants by the alkaline lysis procedure (Birnboim and Doly, Nuc. Acids Res. 7:1513–1523 (1979)). A portion of the DNA from these samples was cut with Pst I and Hind III and analyzed on a 4% polyacrylamide gel to identify clones that released an 80 bp Pst I-Hind III fragment. Other diagnostic cuts, such as Eco RI and Not I, were also made. One of the isolates, designated pGEMT, was shown by restriction analysis to contain the T7 terminator fragment.

TABLE 1

Oligonucleotide Sequences (5'–3')

Figure 1B:
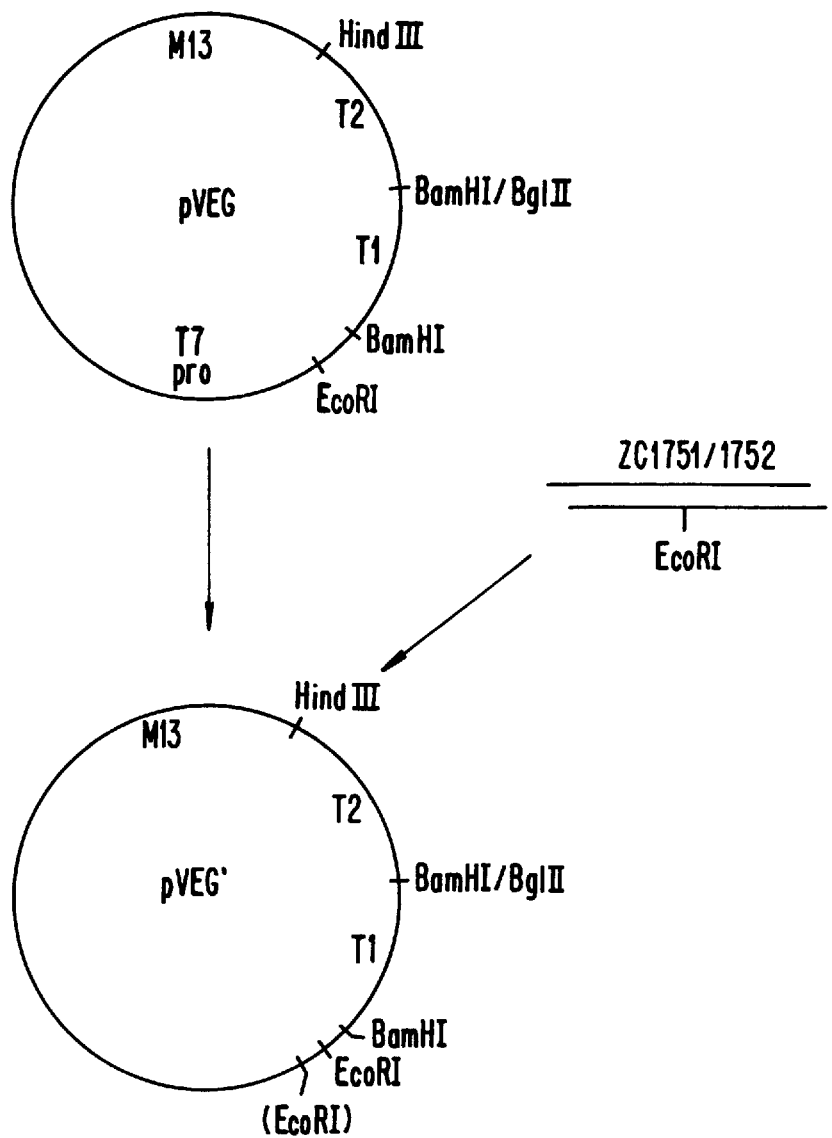
FIG. 1B shows the construction of pVEG' and FIG. 1C shows pVEGT. Symbols used are T7 pro, the T7 promoter; T1 and T2, synthetic and native T7 terminators, respectively; M13, M13 intergenic region; the parentheses indicate a restriction site destroyed in vector construction; and pA is the *Aspergillus niger* polyadenylate sequence.
Figure 1C:
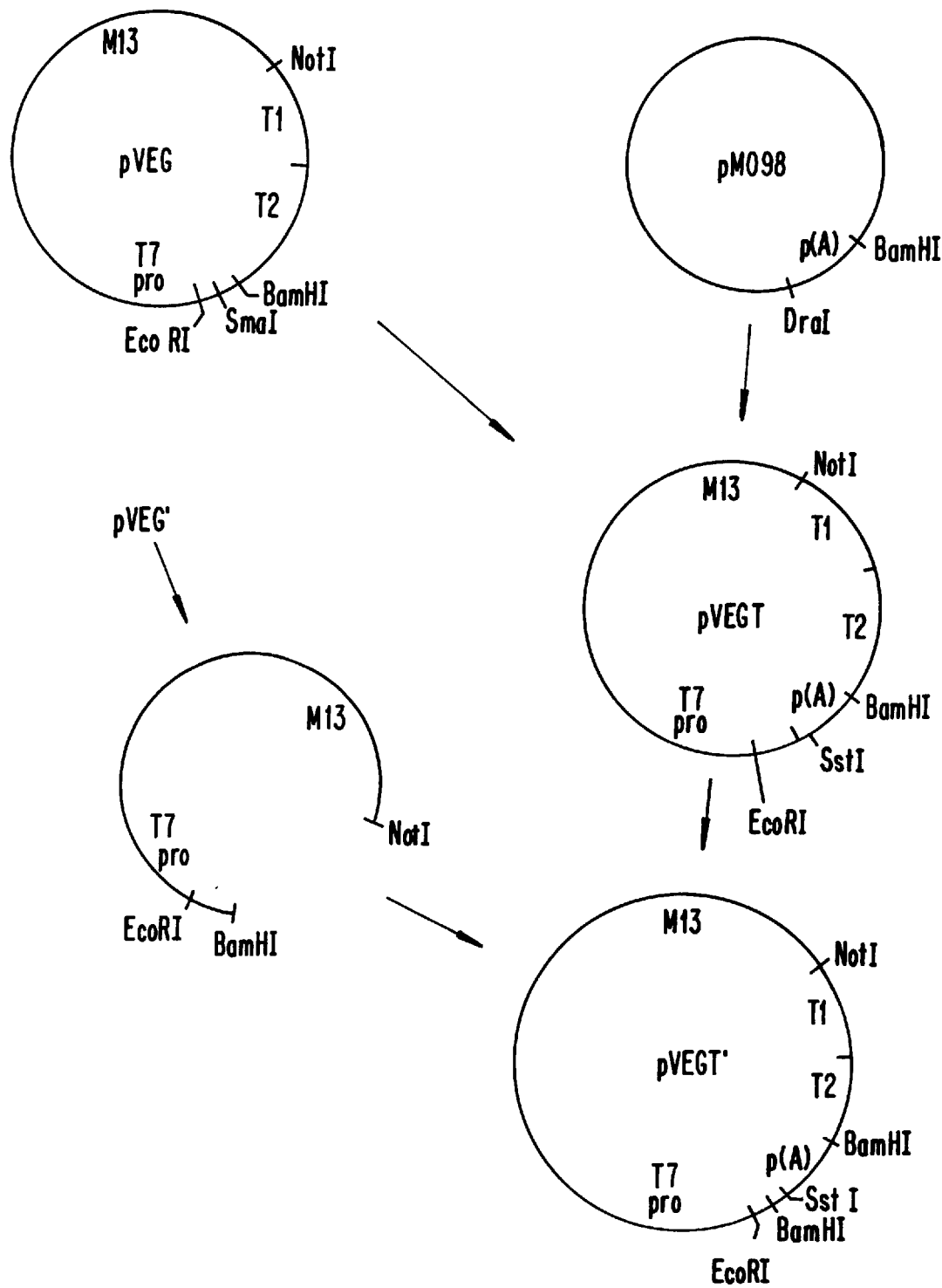

ZC775 (Sequence ID Number 3):
GCT AGC ATA ACC CCT TGG GGC CTC TAA ACG GGT CT
ZC776 (Sequence ID Number 4):
CTC AAG ACC CGT TTA GAG GCC CCA AGG GGT TAT GCT AGC TGC A
ZC777 (Sequence ID Number 5):
TGA GGG GTT TTT TGC TGA AAG GAG GAA CTA TGC GGC CGC A
ZC778 (Sequence ID Number 6):
AGC TTG CGG CCG CAT AGT TCC TCC TTT CAG CAA AAA ACC C
ZC1751 (Sequence ID Number 7):
AAT TCT GTG CTC TGT CAA G
ZC1752 (Sequence ID Number 8):
GAT CCT TGA CAG AGC ACA G
ZC2063 (Sequence ID Number 9):
GAT CCA AAC TAG TAA AAG AGC T
ZC2064 (Sequence ID Number 10):
CTT TTA CTA GTT TG
ZC2938 (Sequence ID Number 11):
GAC AGA GCA CAG ATT CAC TAG TGA GCT CTT TTT TTT TTT TTT T
ZC3015 (Sequence ID Number 12):
TTC CAT GGC ACC GTC AAG GCT
ZC3016 (Sequence ID Number 13):
AGT GAT GGC ATG GAC TGT GGT
ZC3652 (Sequence ID Number 14):
ACA TGC ACC ATG CTC TGT GT
ZC3654 (Sequence ID Number 15):
AGT GAT GGC ATG GAC TGT GGT The native T7 terminator from plasmid pAR2529 (Rosenberg et al., Gene 56:125–135 (1987)) was added to plasmid pGEMT. Plasmid pGEMT was digested with Bam HI and plasmid pAR2529 was digested with Bam HI and Bgl II (FIG. 1). The Bam HI-Bgl II terminator fragment from pAR2529 was purified by agarose gel electrophoresis. The terminator fragment was ligated to Bam HI digested pGEMT, and the DNA was transformed into competent E. coli LM1035 cells. Colonies that were ampicillin resistant were inoculated into 5 ml cultures for overnight growth. Plasmid DNA prepared by the alkaline lysis procedure was screened for proper terminator orientation by Bam HI-Sal I digestion and electrophoresis on an 8% polyacrylamide gel. A clone that contained the terminator in the correct orientation, as evidenced by the presence of a 130 bp Bam HI-Sal I fragment, was chosen and named pGEMTT (FIG. 1).

To allow pGEMTT to be packaged as single-stranded DNA in the presence of M13 phage proteins, the M13 intergenic region from pUC382 (similar to pUC118 and 119 as disclosed by Vieira and Messing, Methods Enzymol. 153: 3–11 (1987)) was added to pGEMTT (FIG. 1). Plasmid pGEMTT was digested with Fsp I and Nar I, and the fragment containing the T7 promoter and transcription terminator was purified. Plasmid pUC382 was digested with Fsp I and Nar I, and the fragment encoding the ampicillin resistance gene and the M13 intergenic region was gel purified. These fragments were then ligated together in the presence of T4 DNA ligase. The ligated DNA was transformed into competent E. coli LM1035 cells. Plasmid DNA from twelve ampicillin-resistant colonies was prepared by the alkaline lysis method, and the DNA was screened by digestion with Ava I. The appropriate construction gave two bands, one of 2430 bp and another of 709 bp. One such isolate was chosen and named pVEG. Synthetic oligonucleotides encoding the prime sequence were added to pVEG between the Bam HI and Eco RI sites (FIG. 1). Plasmid pVEG was digested with Bam HI and Eco RI and the vector fragment was gel purified. Ninety-six nanograms each of oligonucleotides ZC1751 and ZC1752 (Sequence ID Nos. 7 and 8) were annealed in 4.5 μl of 10 mM Tris pH 7.5, 20 mM MgCl$_2$ and 10 mM NaCl at 65° C. for 20 minutes, then the mixture was cooled to room temperature over a period of 30 minutes. The annealed oligonucleotides were ligated to the pVEG vector fragment with T4 DNA ligase and then transformed into competent E. coli LM1035 cells. After growing overnight to develop the colonies, a filter lift was taken of the colonies on the agar plate. The filter was probed with $^{32}$P-labeled oligonucleotide ZC1751 (Sequence ID Number 7). All of the colonies were positive. Plasmid DNA was prepared from cultures grown from 12 of the colonies. The plasmid DNA was screened by digestion with Sst I to verify the absence of the Sst I site between the Eco RI and Bam HI sites of pVEG. All 12 of the plasmid DNAs were negative for Sst I digestion. One of these 12 isolates was chosen and named pVEG'.

A polyadenylate sequence derived from an Aspergillus alcohol dehydrogenase cDNA was added to pVEG. As shown in FIG. 1, plasmid pM098 (disclosed in published European patent application EP 272,277 and deposited with American Type Culture Collection under accession number 53428) was digested with Dra I and Bam HI, and the approximately 150 bp poly(A) fragment was purified by agarose gel electrophoresis. This fragment contained mostly poly(A) sequence with very little flanking cDNA. To clone the poly(A) cDNA fragment into pVEG, pVEG was digested with Bam HI and Sma I, and the 3.4 kb vector fragment was gel purified. The vector and poly(A) fragments were ligated together with T4 DNA ligase to produce vector pVEGT (FIG. 1).

Synthetic oligonucleotides encoding the prime sequence were added to pVEGT. To accomplish this, pVEGT was digested with Not I and Sst I, and the 370 bp fragment containing the poly(A) sequence and the two T7 transcriptional terminators was purified by agarose gel electrophoresis. Plasmid pVEG' was digested with Not I and Bam HI, and the 3.2 kb vector fragment was gel-purified. Two oligonucleotides (ZC2063 and ZC2064; Sequence ID Nos. 9 and 10) that formed, when annealed, a Bam HI-Sst I adapter were synthesized. The two oligonucleotides were individually kinased and annealed, and ligated with the linearized vector and the poly(A)-terminator fragment. The resultant vector, designated pVEGT' (FIG. 1), contained a T7 RNA transcription promoter, an Eco RI cloning site flanked by the prime sequence, a poly(A) tract, and two T7 RNA polymerase terminators.

Construction of cDNA library from rat cerebellum poly (A)+ RNA

Because there was evidence suggesting that the $Glu_GR$ was encoded a very large mRNA of 7 kb (Fong, Davidson, and Lester, *Synapse* 2:657 (1988)) and because full length cDNA encompassing the coding sequence is required for functional cloning of cDNA, measures were taken to optimize for synthesis of large cDNA. A novel method of cDNA synthesis was developed which yielded large full length cDNA. This was evident by demonstration that full length 7.5 kb cDNA could be synthesized from a model 7.5 kb mRNA and that large full length cDNA were present in a library constructed from poly (A)+ RNA as demonstrated by Southern blot analysis. In addition, all enzymes which were important in this method were pretested and selected from a large number of lots of enzymes available from commercial suppliers. Once a satisfactory lot was identified, a large amount of the enzyme was purchased and the enzyme was stored at −70° C. until used. Once used, the enzyme was stored at −20° C. for a few months and then discarded. Different "lots" of enzymes from commercial suppliers, including lots of Superscript reverse transcriptase (BRL), *E. coli* DNA polymerase I (Amersham) and Mung bean nuclease (NEB), which were used in the cDNA synthesis, were screened for quality in test synthesis assays. Superscript reverse transcriptase lots were assayed for the ability to synthesize unit length (7.5 kb) first strand cDNA from 7.5 kb RNA (BRL) control. Conditions for first strand synthesis with Superscript reverse transcriptase lots were prepared as described below. Radiolabeled first strand cDNA was analyzed by alkaline agarose gel electrophoresis. Superscript lots capable of producing unit length, 7.5 kb cDNA were selected for use.

*E. coli* DNA polymerase I lots were assayed for the ability to produce, by hairpin DNA formation, full-length second strand cDNA from the 7.5 kb unit-length first strand cDNA. The second strand cDNA syntheses were carried out as described below. The quality of the second strand syntheses were assessed by alkaline agarose electrophoresis of the radiolabeled product. DNA polymerase I lots capable of producing 15 kb second strand DNA from the 7.5 kb unit length first strand cDNA were selected for use.

Mung bean nuclease lots were tested for the ability to clip the hairpin DNA formed during second strand synthesis without degrading the cDNA. In addition, varying concentrations of enzyme were added to determine the optimum enzyme concentration for the conditions set forth below. The reactions were assessed by alkaline agarose electrophoresis. Lots and concentrations resulting in the production of 7.5 kb unit length cDNA were selected for use.

Total RNA was prepared from rat cerebella using guanidine isothiocyanate (Chirgwin et al. *Biochemistry* 18:52–94 1979) and CsCl centrifugation (Gilsin et al. *Biochemistry* 13:2633–2637 1974). Poly(A)+ RNA was selected from the total RNA using oligo d(T) cellulose chromatography (Aviv and Leder, *Proc. Natl. Acad. Sci. USA* 69:1408 (1972)).

First strand cDNA was synthesized from one time poly d(T)-selected cerebellum poly(A)+ RNA in two separate reactions. One reaction, containing radiolabeled dATP, was used to assess the quality of first strand synthesis. The second reaction was carried out in the absence of radiolabeled dATP and was used, in part, to assess the quality of second strand synthesis. Superscript reverse transcriptase (BRL) was used specifically as described below. A 2.5× reaction mix was prepared at room temperature by mixing, in order, 10 μl of 5× reverse transcriptase buffer (BRL; 250 mM Tris-HCl pH 8.3, 375 mM KCl, and 15 mM $MgCl_2$), 2.5 μl 200 mM dithiothreitol (made fresh or stored in aliquots at −70° C.) and 2.5 μl of a deoxynucleotide triphosphate solution containing 10 mM each of dATP, dGTP, dTTP and 5-methyl dCTP (Pharmacia). The reaction mix was aliquoted into two tubes of 7.5 μl each. To the first tube, 1.3 μl of 10 μCi/μl $\alpha^{32}$P-dATP (Amersham) was added and 1.3 μl of water was added to the second reaction tube. Seven microliters from each tube was transferred to reaction tubes. Fourteen microliters of a solution containing 10 μg of cerebellum poly (A)+ RNA diluted in 14 μl of 5 mM Tris-HCl pH 7.4, 50 μM EDTA was mixed with 2 μl of 1 μg/μl first strand primer, ZC2938 (Table 1; Sequence ID No. 11), and the primer was annealed to the RNA by heating the mixture to 65° C. for 4 minutes, followed by chilling in ice water. Eight microliters of the RNA-primer mixture was added to each of the two reaction tubes followed by 5 μl of 200 U/μl Superscript reverse transcriptase (BRL). The reactions were mixed gently, and the tubes were incubated at 45° C. for 30 minutes. After incubation, 80 μl of 10 mM Tris-HCl pH 7.4, 1 mM EDTA was added to each tube, the samples were vortexed and centrifuged briefly. Three microliters of each reaction was removed to determine total counts and TCA precipitable counts (incorporated counts). Two microliters of each sample was analyzed by alkaline gel electrophoresis to assess the quality of first strand synthesis. The remainder of each sample was ethanol precipitated. The nucleic acids were pelleted by centrifugation, washed with 80% ethanol and air dried for ten minutes. The first strand synthesis yielded 1.4 μg of cerebellum cDNA or a 28% conversion of RNA into DNA.

Second strand cDNA synthesis was performed on the RNA-DNA hybrid from the first strand reactions under conditions which encouraged first strand priming of second strand synthesis resulting in DNA hairpin formation. The nucleic acid pellets containing the first strand cDNA were resuspended in 71 μl of water. To assess the quality of second strand synthesis, $\alpha^{32}$P-dATP was added to the unlabeled first strand cDNA. To encourage formation of the hairpin structure, all reagents except the enzymes were brought to room temperature, and the reaction mixtures were set up at room temperature. (Alternatively, the reagents can be on ice and the reaction mixture set up at room temperature and allowed to equilibrate at room temperature for a short time prior to incubation at 16° C.) Two reaction tubes were set up for each synthesis. One reaction tube contained the unlabeled first strand cDNA and the other reaction tube contained the radiolabeled first strand cDNA. To each reaction tube, 20 μl of 5× second strand buffer (100 mM Tris, pH 7.4, 450 mM KCl, 23 mM $MgCl_2$, 50 mM $(NH_4)_2SO_4$), 3 μl of beta-NAD and 1 μl of a deoxynucleotide triphosphate solution containing 10 mM each of dATP, dGTP, dTTP and dCTP (Pharmacia), 1 μl $\alpha^{32}$P-dATP or 1 μl of water (the radiolabeled dATP was added to the tube containing the unlabeled first strand cDNA), 0.6 μl of 7 U/μl *E. coli* DNA ligase (Boehringer-Mannheim), 3.1 μl of 8 U/μl *E. coli* DNA polymerase I (Amersham), and 1 μl of 2 U/μl of RNase H (BRL). The reactions were incubated at 16° C. for 2 hours. After incubation, 3 μl was taken from each reaction tube to determine total and TCA precipitable counts. Two microliters of each sample was analyzed by alkaline gel electrophoresis to assess the quality of second strand synthesis by the presence of a band of approximately twice unit length. To the remainder of each sample, 2 µl of 2.5 µg/µl oyster glycogen, 5 µl of 0.5M EDTA and 200 µl of 10 mM Tris-HCl pH 7.4, 1 mM EDTA were added, the samples were phenol-chloroform extracted, and isopropanol precipitated. The nucleic acids were pelleted by centrifugation, washed with 80% ethanol and air dried. The yield of double stranded cDNA in each of the reactions was approximately 2 µg.

The single-stranded DNA in the hairpin structure was clipped using mung bean nuclease. Each second strand DNA sample was resuspended in 12 µl of water. Two microliters of 10× mung bean buffer (0.3M NaOAC, pH 4.6, 3M NaCl, 10 mM ZnSO$_4$), 2 µl of 10 mM dithiothreitol, 2 µl of 50% glycerol, and 2 µl of 10 U/µl mung bean nuclease (NEB, lot 7) were added to each tube, and the reactions were incubated at 30° C. for 30 minutes. After incubation, 80 µl of 10 mM Tris-HCl pH 7.4, 1 mM EDTA was added to each tube, and 2 µl of each sample was subjected to alkaline gel electrophoresis to assess the cleavage of the second strand product into unit length cDNA. One hundred microliters of 1M Tris-HCl pH 7.4 was added to each sample, and the samples were twice extracted with phenol-chloroform. Following the final phenol-chloroform extraction, the DNA was isopropanol precipitated. The DNA was pelleted by centrifugation, washed with 80% ethanol and air dried. Approximately 2 µg of DNA was obtained from each reaction.

The cDNA was blunt-ended with T4 DNA polymerase after the cDNA pellets were resuspended in 12 µl of water. Two microliters of 10× T4 DNA polymerase buffer (330 mM Tris-acetate, pH 7.9, 670 mM KAc, 100 mM MgAc, 1 mg/ml gelatin), 2 µl of 1 mM dNTP, 2 µl 50 mM dithiothreitol, and 2 µl of 1 U/µl T4 DNA polymerase (Boehringer-Mannheim) were added to each tube. After an incubation at 15° C. for 1 hour, 180 µl of 10 mM Tris-HCl pH 7.4, 1 mM EDTA was added to each sample, and the samples were phenol-chloroform extracted followed by isopropanol precipitation. The cDNA was pelleted by centrifugation, washed with 80% ethanol and air dried. Eco RI adapters (Invitrogen, Cat. # N409-20) were ligated to the blunted cDNA after the DNA from each reaction was resuspended in 6.5 µl water.

The first strand primer encoded an Sst I cloning site to allow the cDNA to be directionally cloned into an expression vector. The cDNA was digested with Sst I followed by phenol-chloroform extraction and isopropanol precipitation. After digestion, the cDNA was electrophoresed in a 0.8% low melt agarose gel, and the cDNA over 4.2 kb was electroeluted using an Elutrap (Schleicher and Schuell, Keene, N.H.). The electroeluted cDNA in 500 µl of buffer was isopropanol precipitated and the cDNA was pelleted by centrifugation. The cDNA pellet was washed with 80% ethanol.

A cerebellum cDNA library was established by ligating the cDNA to the Eco RI-Sst I digested, agarose gel purified pVEGT'.

Ten sublibraries of one million clones each were constructed representing a library of ten million independent clones. To prepare each sublibrary, 80 ng of linearized vector were ligated to 40 ng of cDNA. After incubation at room temperature for 11 hours, 2.5µg of oyster glycogen and 80 µl of 10 mM Tris-HCl, 1 mM EDTA was added and the sample was phenol-chloroform extracted followed by ethanol precipitation. The DNA was pelleted by centrifugation, and the DNA pellet washed with 80% ethanol. After air drying, the DNA was resuspended in 3 µl of water. Thirty-seven microliters of electroporation-competent DH10B cells (BRL) was added to the DNA and electroporation was completed using a BioRad electroporation unit. After electroporation, 4 ml of SOC (Maniatis et al.) was added to the cells, and 400 µl was spread on each of 10–150 mm LB ampicillin plates. Each plate represented a sublibrary of 100,000 clones. After an overnight incubation, the cells were harvested by adding 10 ml of LB ampicillin media to each plate and scraping the cells into the media. Glycerol stocks and plasmid DNA were prepared from each plate. The library background (vector without insert) was established at about 15%.

Detection of Glu$_G$R activity from the cDNA library

The Xenopus oocyte efficiently translates exogenously added mRNA. Preliminary experiments were done using the mouse m1 muscarinic receptor cDNA (a G protein coupled receptor that can be detected by voltage-clamp) cloned into pVEGT'. Injection of RNA transcribed in vitro from increasing dilutions of the m1 template DNA indicated that m1 agonist induced activity could be detected for one clone in a pool size of 100,000. A cerebellum sublibrary was plated into ten pools of 100,000 unique clones.

The pools could also be replica plated onto a nitrocellulose filter and the original and replica allowed to grow for a few hours. The original plate is scraped to harvest all the colonies. Plasmid DNA is prepared and purified by cesium chloride gradient ultracentrifugation. The DNA from each pool is transcribed in vitro with T7 RNA polymerase in the presence of 7-methyl-G, the capped nucleotide, to increase translation efficiency. Template DNA transcription reactions are spiked with a dilution of two control genes cloned into pVEGT': the mouse m1 gene and a secreted version of the human placental alkaline phosphatase gene (SEAP; Tate et al., Fed. Am. Soc. Exp. Biol. 8: 227–231 (1990), incorporated by reference herein). Transcription from the control genes would allow selection of oocytes that more efficiently translate the injected RNA, and a determination whether oocytes that are negative for the Glu$_G$R are true negatives, that is, still having a detectable m1 agonist-induced response.

Plasmid DNA prepared from each of the 10 pools of 100,000 clones, which in total represented one sublibrary of one million clones of the cerebellum cDNA library, was purified by cesium chloride gradient ultracentrifugation. The DNA was transcribed in vitro with T7 RNA polymerase (Pharmacia) in the presence of capped nucleotide (GpppG, Pharamcia). The presence of a poly (A) sequence and two T7 RNA polymerase terminators in pVEGT' resulted in RNA with a capped 5' end, the sequence of the cDNA insert, and 3' poly (A) tails. Capped RNA is believed necessary for efficient translation in oocytes (Noma et al. Nature 319:640 (1986)) and the poly (A) sequence has been shown to increase the synthesis of a protein in oocytes by more then 40 fold. The transcription reaction tubes were set up by adding 12 µl of 5× transcription buffer (Stratagene Cloning Systems, La Jolla, Calif.), 3 µl each of 10 mM ATP, CTP, GTP, and UTP, 6 µl of 10 mM GpppG (Pharmacia), 6 µl of 1 mg/ml BSA, 3 µl of 200 mM DTT, 1.5 µl of 40 U/µl RNasin (ProMega Biotech, Madison, Wis.), 8.5 µl of water, 10 µl of cDNA containing 5 to 10 µg DNA, and 1 µl of 70 U/µl T7 RNA polymerase. After mixing, 10 µl of the reaction was transferred to a tube containing 0.5 µCi of α$^{32}$P-UTP to determine the total counts and counts incorporated into RNA. The samples were incubated at 37° C. for one hour. The cDNA in the unlabeled samples was degraded with the addition of 1 µl of 200 mM DTT, 2 µl of 30 U/µl DNase I, and 0.5 µl of 40 U/µl RNasin and the incubation was continued at 37° C. for 15 minutes. Forty microliters of water was added to the radiolabeled reactions, and 1 μl was removed from each sample and counted to determine total counts. The remainder of the labeled samples were ethanol precipitated. The samples were centrifuged to collect the RNA and the RNA pellets were counted to determine the counts incorporated into RNA. After the DNA degradation reaction in the unlabeled samples, 70 μl of 10 mM Tris-HCl, 1 mM EDTA was added to each sample, and the samples were twice-extracted with phenol-chloroform followed by one chloroform extraction. The RNA was ethanol precipitated. After centrifugation to collect the RNA, the pellets were washed with 80% ethanol, followed by air drying for 10 minutes. A typical yield of the unlabeled RNA was 20 to 30 μg. The unlabeled RNA was resuspended at 2 μg/μl in diethylpyrocarbonate (DEPC, Sigma) treated water and stored at −70° C.

Prior to microinjection into oocytes, the RNA samples were thawed and centrifuged in a microfuge for 5 minutes to remove any particles that might clog a microinjection pipet. After centrifugation, 80% of each sample was removed and split into two tubes.

The RNA from each of the 10 sublibraries were injected into oocytes as described above and translation was allowed for four days. Expression of $Glu_GR$ activity was assessed by voltage-clamp assay as described above. One of the 10 sublibraries, Z93-1.9, produced a signal with administration of quisqualate to the oocyte.

Subdivision of the cDNA library pool to obtain pure $Glu_GR$ clone

The DNA pool (Z93-1.9) was subdivided by plating clones from the glycerol stock onto LB ampicillin plates. To determine the number of clones that should be plated for the subdivision of the 100,000 clone pool to identify a positive clone, the probability equation $N=\ln(1-P)/\ln(1-f)$ (Maniatis et al., ibid.) was used, where P is the desired probability of including the clone of interest, f is the fraction of positive clones in the pool, and N is the number of clones to be plated to provide the given probability. For a probability of 99.8% for a pool size of 100,000 to contain one positive clone, 621,461 clones should be plated.

Forty-eight 150 mm LB ampicillin plates were plated with the glycerol stock representing the 100,000 positive pool, Z93-1.9, at a density of approximately 14,000 clones per plate to give a total of 670,000 clones. After an overnight incubation 37° C., the bacteria on each plate were harvested into 10 ml of Solution I (as described by Birnboim and Doly, *Nuc. Acids Res.* 7:1513 (1979)), incorporated by reference herein). A glycerol stock was prepared from a portion of the cells, and plasmid DNA was prepared from the remainder of the cells. Six pools of DNA representing eight of the LB ampicillin plates each were prepared by combining one tenth of the plasmid DNA from groups of eight plates into each pool. The plasmid DNA from these six pools was purified by cesium chloride gradient centrifugation. The DNA was transcribed into RNA as outlined above. Transcription of the parent pool Z95-1.9 was included as the positive control. Oocytes were injected with the RNA and voltage-clamp assays on the oocytes identified pool Z99-25-32 as positive for $Glu_GR$. Pool Z99-25-32 contained DNA prepared from plates 25 through 32.

Plasmid DNA from plates 25 to 32 were cesium chloride banded and transcribed into RNA as described above along with the positive parent pool Z99-25-32. Oocytes were injected with the RNA and voltage clamp assays, carried out as described above, identified pools Z104-25 and Z1111-32 as being weakly positive, Z106-27 and Z109-30 as intermediately positive, and Z108-29 and Z110-31 as the most positive. The pool resulting in Z110-31 was chosen for further subdivision.

Identification of positive pools from the subdivision of the positive pool of 14,000 (Z110-31) from the glycerol stock was unsuccessful. Therefore, plasmid DNA prepared from the pool resulting in Z110-31 was electroporated into bacteria and plated on 60 plates at a density of 1,000 clones/plate. Plasmid DNA was prepared from the bacteria harvested from each plate. Aliquots of the plasmid DNA from each plate were mixed to make six pools representing ten plates each. The plasmid DNA was cesium chloride banded, and the RNA was transcribed as described above. RNA was transcribed from pools Z108-29, Z110-31, and a muscarinic receptor cDNA, m1, for use as positive controls. The RNA was injected into oocytes and voltage-clamp assays were carried out as described above. The assays identified pool Z133-21 to 30 as positive.

Plasmid DNA from plates 21 to 30 were cesium chloride banded and transcribed as described above. The transcribed RNA and the RNA from the parent pool Z133-21 to 30 were injected into oocytes and assayed as described above. The voltage-clamp assay identified pool Z142-22 as positive.

Identification of positive pools by the subdivision of the positive pool Z142-22 from a glycerol stock proved unsuccessful. Restriction analysis of plasmid DNA prepared from randomly selected clones from pools Z110-31 (the pool of 14,000) and Z142-22 (the pool of 1,000) indicated that 50% of pool Z110-31 and 68% of pool Z142-22 were clones without inserts.

To assess physical methods for enriching for the $Glu_GR$ clone and to establish how many clones from pool Z142-22 needed to be assayed to include a $Glu_GR$ clone, undigested plasmid DNA from pool Z142-22 was electrophoresed on an agarose gel. The super-coil band representing vector without insert was cut out and the remainder of the DNA was eluted from the gel. The DNA was then electroporated into bacteria cells, and plated at densities of 3,400, 6,900, and 13,800 clones per plate. The plates were replica plated and grown overnight. Plasmid DNA was prepared from the cells harvested from the replica of each plate. The plasmid DNA was transcribed, and the RNA was assayed in oocytes as described above. As a control, each pool contained the equivalent of one colony of m1 as an internal positive control. In addition, m1 was used as an external positive control. The voltage-clamp assays identified the DNA from the 6,900 clone pool (Z167-7) as positive.

The clones represented on the 6,900 clone plate that resulted in the positive pool Z167-7 were subdivided by replica plating the master plate onto a BIOTRANS nylon memberane (ICN Flow, Costa Mesa, Calif.) on an LB ampicillin plate. The replica plate was incubated four hours at 37° C. After incubation, sub-pools were prepared by removing the membrane from the plate, taping the membrane to a sterile glass plate on a light box, and overlaying the membrane with a grid which divided the membrane into 100 sections. The sections of the grid and underlying membrane were then cut out with a razor blade that had been dipped in alcohol and flamed between each cut. Alcohol-treated, flamed forceps were used to transfer each membrane section to a test tube containing 12.5 ml of LB ampicillin media. The cultures containing the membrane sections were incubated overnight at 37° C. After incubation, 0.5 ml of each culture was mixed with 0.5 ml of 50% glycerol and stored at −70° C. to establish glycerol stocks of each sub-pool. Aliquots of the 100 cultures were pooled in a 10×10 matrix with samples (1) through (10) on the abscissa and samples (a) through (j) on the ordinate. For example, 1 ml of cultures (1) through (10) were added to tube 1 and 1 ml of cultures (1), (11), (21), (31), (41), (51), (61), (71), (81), and (91) were added to tube (a) and so on until 10 rows of 10 and 10 columns containing pools of 10 cultures each were completed. Ten microliters of an overnight culture containing m1-transformed bacteria was added to each pool as an internal control. Plasmid DNA was prepared from the 20 sub-pools, and the DNA was purified by cesium chloride gradient centrifugation. RNA was transcribed from the plasmid DNA and was assayed in oocytes as described above. Positive controls were the parent pool Z167-7 and pure m1 RNA. The voltage-clamp assays indicated that only pools Z175-1 and Z191-g were positive. Consulting the matrix, this indicated that the membrane section number (7) contained the $Glu_GR$ clone.

To subdivide the clones contained in section (7), a piece of Biodyne A membrane was applied to the master plate containing section (7), the membrane extending beyond section (7) on each side by half the width of section (7). The membrane was removed from the plate, applied to a fresh LB ampicillin plate colony side up, and incubated overnight at 37° C. The membrane was subdivided as described above with the central region of the membrane, the actual section (7) area, divided into 9 small, equivalent-sized squares and the membrane on each side of section (7) was taken as four additional areas. Each membrane section was used to inoculate a 10 ml liquid culture. Bacteria transformed with the m1 clone were used as an internal control in each culture as described above. After overnight incubation at 37° C., plasmid DNA was prepared, and the DNA was purified by cesium chloride gradient centrifugation. RNA was transcribed and assayed in oocytes as described above using RNA from m1 and the parent pool number (7) as positive controls. $Glu_GR$ activity was found in only pool Z203-7 corresponding to membrane section number (7).

Pool Z203-7 was subdivided by electroporating the plasmid DNA prepared from the membrane section number (7) into DH10B electroporation-competent cells. The transformants were plated at a density enabling individual colonies to be picked. Individuals clones were picked to a master plate and into 2 ml of LB ampicillin media. The cultures were incubated overnight, and plasmid DNA was prepared by the method essentially described by Holms and Quigley (*Anal. Bioc.* 114: 193, (1981)). Restriction analysis suggested that the clones were grouped into 7 different classes of clones. Plasmid DNA, prepared from each class, representing fifty total clones were prepared, transcribed, and assayed in oocytes as described above. However, none of the clones were positive.

To screen for positive clones, electroporation-competent *E. coli* DH10B cells were electroporated with the DNA prepared from membrane section number (7) (Z203-7) and were plated at 180, 360, 900, and 1800 colonies per plate. The plates were incubated overnight, and replica plates were prepared as described above. Plasmid DNA prepared from each replica plate was combined with 1 to 1000 parts of m1 as an internal control. The DNA pools, the m1 clone and the parent pool Z203-7 were transcribed, and the RNA was assayed by oocyte injection. The first transcription and injection showed no positives, however, upon retranscription and reanalysis the 1800 clone pool (Z264-1800) was positive for $Glu_GR$ activity.

To subdivide the positive pool of 1800 (Z264-1800), all of the colonies from the plate of 1800, 1528 in total, were each picked to two sets of 100 mm LB ampicillin agar plates on a 100 colony grid. After overnight growth, one set of the duplicate plates was designated as a master set and was placed at 4° C. The other set was replica plated to a third set of plates. After overnight incubation of these plates, the cells on the replica plates were harvested into media and plasmid DNA was prepared from the pooled cells. As described above, an internal m1 control was included in each DNA preparation. m1 DNA and the parent Z264-1800 DNA were used as external positive controls. Plasmid DNA prepared from the 16 plates was transcribed, and the RNA was assayed in oocytes as described above. One of the pools of 100 clones, Z256-I produced $Glu_GR$ activity.

To identify which clone of the 100 clones from Z256-I produced the $Glu_GR$ activity, a 10×10 matrix of the clones was constructed. A liquid culture of each clone was grown. One milliliter of each culture was added to each of two tubes representing the appropriate row and column of the 10×10 matrix. As described previously, plasmid DNA encoding m1 was used as an internal positive control. Plasmid DNA prepared from each tube, m1 DNA and DNA from the parent pool Z264-1800 were transcribed and assayed in oocytes as described above. $Glu_GR$ activity was identified only in row (5) and column (e). Thus, the positive clone number 45 was identified as containing the $Glu_GR$ activity.

To confirm the result, plasmid DNA from clone #45 was prepared, transcribed and assayed in oocytes as described above. The results of the assay indicated that clone #45 was capable of producing $Glu_GR$ activity. FIG. 2 illustrates the data taken from voltage-clamp recordings at several stages in the subfractionation of the cerebellum library. Panel (a) is a recorded response to quisqualate of an oocyte previously injected with in vitro transcribed RNA from a rat cerebellum sublibrary of 100,000 independent colonies; panel (b) shows the response to quisqualate in a cell previously injected with RNA transcribed from a subfractionated pool of 14,000 colonies. The peak current was truncated by the chart recorder, but the actual peak current (estimated from a digital panel meter) was approximately 1300 nA. Panel (c) shows the response to quisqualate in a cell injected with pure $Glu_GR$ RNA from clone 45-A. The amount of RNA injected per oocyte was approximately 100 ng, except in panel (c) where the amount of RNA was 50 pg.

The following describes an alternative means for subdividing and screening a positive pool. Working with cDNA inserts in a plasmid based rather than a lambda-based vector influences the subfractionation protocol. Once a positive pool is identified, the replica filter is overlayed with another sterile nitrocellulose filter. The filter is cut into 88 pieces by using evenly spaced cuts of 10 rows and 10 columns to form a grid. Each of the 88 pieces is transferred to 10 ml of sterile LB +Amp and grown for several hours. Twenty pools are formed; C 1–10 (corresponding to column number) and R 1–10 (corresponding to row number). An aliquot of each of the 88 subfractions is pipetted into 2 tubes, corresponding to its position in a row and a column. DNA is isolated from the 20 pools, purified on CsCl gradients and transcribed in an in vitro reaction that includes the control m1 and SEAP plasmids. After injection into oocytes and voltage-clamp recording there are 2 positive pools, pinpointing the location of 1 of the 88 original subfractions.

Because the positive clone is still part of a pool it must be further subdivided. The probability equation described above is used to determine the number of clones to be plated for the next subdivision of the pool. The glycerol stock from the positive pool is plated out at, e.g., 3000, 6000 and 18,000 clones per plate. After replica plating the DNA is harvested, transcribed, injected and assayed. The pool which is positive is subdivided into a grid of 88 as described above. The assay is repeated, and a single square of the grid is positive. At the next step of subdivision of the pool, 100 individual colonies to a plate are picked, replica plated, and 20 pools are made for transcription and assay. Positive clones are streaked out, several colonies picked and restriction mapped and template and transcript prepared for injection and assay.

Characterization of $Glu_GR$

To establish that the $Glu_GR$ encoded by clone 45-A couples to G-protein, clone 45-A $Glu_GR$ RNA was transcribed and injected into oocytes as described above. Two days after injection the oocytes were divided into control and toxin-treated groups. The oocytes in the toxin-treated group were treated with a final concentration of 4 µg/ml of *B. pertussis* toxin (List Biological Laboratories Inc., Campbell, Calif.), and both groups were incubated for 24 hours at 19° C. as described by Sugiyama et al., *Nature* 325:531 (1987) and Moriarity et al., *J. Biol. Chem.* 264:13521 (1989), both of which are incorporated by reference herein. The oocytes from both the control and toxin-treated groups were subjected to voltage-clamp assays as described previously. In one example, oocytes perfused as described previously with 100 µM L-glutamic acid showed a mean L-glutamic acid-induced current of 264.2 nA±73 nA in control oocytes (SEM, n=6) and 57.7 nA±19 nA (n=9) in toxin-treated oocytes. The mean membrane current in the toxin-treated group was significantly smaller (p<0.01) than in the control group suggesting that oocytes injected with 45-A RNA coupled to a pertussis toxin-sensitive G protein.

L-glutamic acid and some of its structural derivatives that are known to activate $Glu_GR$ currents in a dose-dependent manner were applied to oocytes that had been injected with RNA transcribed from the 45-A clone. RNA was transcribed and oocytes were prepared and injected as previously described. Dose dependent responses were measured using voltage clamp assays were carried out in the presence of increasing concentrations of L-glutamic acid (Sigma), quisqualic acid (Sigma), ibotenic acid (Sigma), or trans 1-amino-cyclopentyl-1,3 dicarboxylic acid (tACPD; Tocris Neuramin, Essex, England). Four or five separate oocytes were perfused with increasing concentrations of a particular drug with 30 minutes between consecutive applications of the drug to minimize any interference from desensitization. The responses were normalized to a subsequent response to 100 µM L-glutamic acid. The data were analyzed using the following equation:

$$(\text{Fractional current}) = (\text{Dose}^n)/(\text{Dose}^n) + (EC_{50})^n,$$

where:

Dose=a dose of drug normalized to that evoked by a subsequent application of 100 µM L-glutamic acid;

Fractional current=the peak current evoked by a dose, as defined above;

$EC_{50}$=effective concentration that evokes a 50% response (a measure of the potency of an agonist); and n=the Hill coefficient, a measure of the cooperativity of the reaction.

Figure 6:
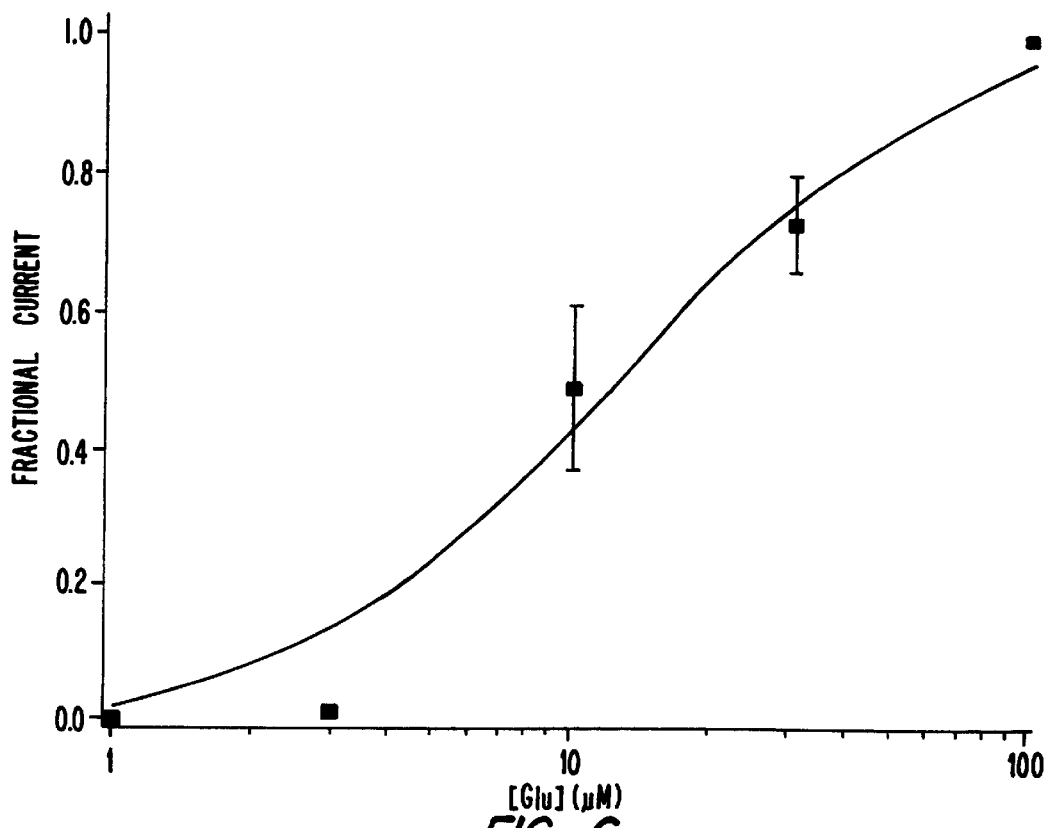
FIG. 6 illustrates a representative dose response curve for varying concentrations of L-glutamic acid. Error bars, where larger that the symbols represent SEM.

Using this equation, the effective concentration at 50% stimulation relative to 100 µM L-glutamic acid was determined for each dose response experiment. FIG. 6 shows a representative dose response curve for varying concentrations of L-glutamic acid. The potency series of glutamate analogs and their associated $EC_{50}$'s are listed in Table 2.

TABLE 2

| Glutamate Analog Potencies ($EC_{50}$) | |
|---|---|
| Quisqualic acid | 0.681 µM |
| L-glutamic acid | 12.32 µM |
| Ibotenic acid | 32.37 µM |
| tACPD | 376 µM |

In addition, oocytes were exposed to the following L-glutamic acid analogs: aspartic acid (Tocris Neuramin), kainic acid, N-methyl-D-aspartic acid (NMDA; Sigma), 2-amino-4-phosphonobytyric acid (APB; Sigma), α-amino-3-hydroxy-5-methyl-isoxazole-4-propionic acid (AMPA; Research Biochemicals Inc., Wayland, Mass.) at saturating concentrations and the responses were each normalized to a subsequent response to 100 µM L-glutamate. The L-glutamic acid analogs that were found to be ineffective were 1 mM aspartic acid, 1 mM kainic acid, 100 µM NMDA+10 µM glycine, 100 µM APB and 100 µM AMPA.

Voltage clamp assays were also carried out on injected oocytes to measure the inhibition by the putative glutamate G protein coupled receptor antagonist, 2-amino-3-phosphonopropionic acid (AP3). Voltage clamp assays showed that at 1 mM, DL-AP3 (Sigma) reduced the current evoked by 10 µM glutamic acid to 59.3±7.3% of the control.

Figure 3:
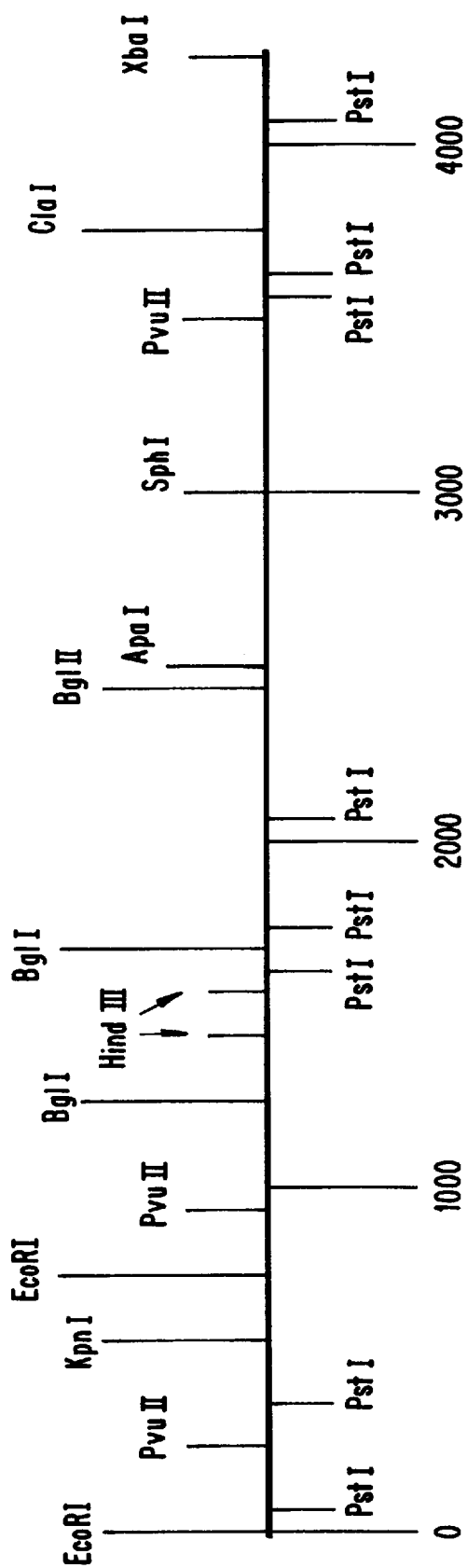
FIG. 3 illustrates a partial restriction map of clone 45-A.

Clone 45 cells were streaked out on LB Amp plates and several colonies were picked, grown up and the DNA isolated. Pure 45-A DNA was prepared and restriction mapped by standard procedures. Clone 45-A has been deposited with the American Type Culture Collection, 12301 Parklawn Drive, Rockville, Md., 20852, under ATCC Accession No. 68497. DNA was digested with single or multiple enzymes. The fragments were separated on both 1% agarose and 4% Nusieve gels by electrophoresis. After electrophoresis the DNA was transferred to nitrocellulose filters using standard protocols for Southern transfer. Restriction sites were mapped based on size and based on hybridization to Pst I subclones of 45-A DNA. Additionally, the entire 45-A cDNA insert can be isolated by digestion with Not I restriction endonuclease. The Not I insert was kinased with $^{32}$-P ATP, and after digestion of half of the sample with Bam HI to remove the 3' label, both samples were subjected to digestion with a number of enzymes known to be present once in the insert. In this way the unique sites could be localized. A restriction map of $Glu_GR$ clone 45-A is shown in FIG. 3.

The entire 45-A clone was sequenced in both directions using the dideoxynucleotide chain termination method (Sanger and Coulson, *J. Mol. Biol.* 94:441 (1975), incorporated herein by reference). FIG. 5 (Sequence ID Nos. 1 and 2) shows the DNA sequence and deduced amino acid sequence of clone 45-A. FIG. 5 also shows the location of putative N-linked glycosylation sites, which have been predicted to occur at the amino acid sequence Asn-X-Thr.

As shown in FIG. 5, seven putative transmembrane domains have been predicted from the deduced amino acid sequence of clone 45-A using the method described by Eisenberg et al. *J. Mol. Biol.* 179:125–142, (1984), incorporated herein by reference. Only those predicted to be transmembrane multimeric domains were included. An additional transmembrane domain (the third) was predicted using the method of Hopp and Woods, *Proc. Natl. Acad. Sci. USA* 78:3824–3838 (1981). Based on these predictions, the protein encoded by clone 45-A appears to have two unusually large domains on the amino- and carboxy-termini that are not found in any of the other reported G protein coupled receptors which have the common structural feature of seven predicted membrane spanning regions. Analysis of the deduced amino acid sequence of clone 45-A predicts three other hydrophobic stretches including one at the amino-terminus of the sequence. This amino-terminal hydrophobic stretch may be a signal sequence, although no signal cleavage site is predicted downstream of the sequence.

Poly (A)+ RNA was isolated from total rat brain and rat cerebellum using oligo d(T) cellulose chromatography as described by Aviv and Leder (ibid.). Poly (A)+ RNA from rat retina, rat heart, rat lung, rat liver, rat kidney, rat spleen, rat testis, rat ovary and rat pancreas were purchased from Clonetech. The poly(A)+ RNA samples were analyzed by northern analysis (Thomas, *Proc. Natl. Acad. Sci. USA* 77:5201–5205 (1980), which is incorporated by reference herein). The RNA was denatured in glyoxal, electrophoresed in agarose and transferred to a nitrocellulose membrane essentially as described by Thomas (ibid.). The northern blot was hybridized with a radiolabeled 3473 bp Eco RI-Xba I fragment from the 45-A clone. Autoradiography of the blot showed hybridization to a major band of approximately 7 kb and a smaller band of approximately 3.8 kb in the total rat brain and rat cerebellum RNA.

Single-stranded cDNA was synthesized using 1 μg of the poly (A)+ RNA using Superscript reverse transcriptase (BRL) under conditions described by the manufacturer. One fourth of the cDNA was used as a template for PCR amplification using 40 pmoles each of the GluGR-specific primers ZC3652 (Table 1; Sequence ID Number 14) and ZC3654 (Table 1; Sequence ID Number 15) and 2.5 U Taq I polymerase (Perkin Elmer Cetus, Norwalk, Va.) and conditions specified by the manufacturer. As an internal control, the PCR reaction also contained 2 pmoles each of the glucose-6-phosphate dehydrogenase-specific primers ZC3015 (Table 1; Sequence ID Number 12) and ZC3016 (Table 1; Sequence ID Number 13). After thirty cycles (one minute at 94° C., one minute at 60° C., ninety seconds at 72° C.), the samples were phenol-chloroform extracted and 20% of each reaction was electrophoresed in agarose. The DNA was bidirectionally transferred to nitrocellulose membranes, and the filters were hybridized with either radiolabeled ZC3652, ZC3654, ZC3015 and ZC3016 (Sequence ID Nos. 14, 15, 12 and 13, respectively) or with the radiolabeled Eco RI-Xba I fragment of clone 45-A described above. Autoradiography of the hybridized blot showed that $Glu_GR$ transcript was mainly confined to total rat brain and rat cerebellum; however, longer exposures showed a $Glu_GR$-specific transcript in both retina and testis.

Total RNA was prepared, as described above, from specific rat brain regions including frontal cortex, cerebellum, hippocampus, cortex, striatum, pons medulla, and the remainder of the brain. Single-stranded cDNA was synthesized as described previously using 20 μg of total RNA in 50 μl using Superscript reverse transcriptase (BRL) under conditions described by the manufacturer. After a one hour incubation at 42° C., the samples were treated with RNAse (Boehringer Mannheim Biochemicals, Indianapolis, Ind.), phenol-chloroform extracted, and ethanol precipitated. The samples were resuspended in water and half of each sample was subjected to PCR amplification. Each PCR amplification contained 40 pmoles of each of the $Glu_GR$-specific primers ZC3652 and ZC3654 described above (Sequence ID Numbers 14 and 15), 2 pmoles of each of the glucose-6-phosphate dehydrogenase-specific primers ZC3015 and ZC3016 (Sequence ID Nos. 12 and 13) and 2.5 U Taq I polymerase (Perkin Elmer Cetus) and conditions described by the manufacturer. After 35 cycles (one minute at 94° C., one minute at 60° C., ninety seconds at 72° C.), the samples were phenol-chloroform extracted, and 20% of each reaction was electrophoresed in agarose. The DNA was transferred to a nitrocellulose membrane, and the filter was hybridized with the radiolabeled Eco RI-Xba I fragment of clone 45-A described above. Autoradiography of the hybridized blots showed a broad distribution of the $Glu_GR$ transcript throughout the brain, although the frontal cortex and cerebellum appear to be somewhat enriched.

Southern analysis of rat and human genomic DNA was carried out using the method essentially described by Blin et al. (*Nuc. Acids Res.* 3:2303 (1976), which is incorporated by reference herein). Briefly, rat and human genomic DNA was prepared from the rat cell line UMR 106 (ATCC CRL 1661) and a human hepatoma cell line (ATCC HTB 52), respectively. The genomic DNA was digested with either Eco RI or Pst I, and electrophoresed through agarose. The DNA was transferred to a nitrocellulose membrane, and the membrane was hybridized with a radiolabeled 1.6 kb Pst I fragment from clone 45-A. Autoradiography of the hybridized blot suggest that the human gene has a similar sequence to the rat $Glu_GR$ sequence, the $Glu_GR$ gene contains at least one intron, and that there are a small number of closely related genes.

Expression in Mammalian Cells

Figure 4:
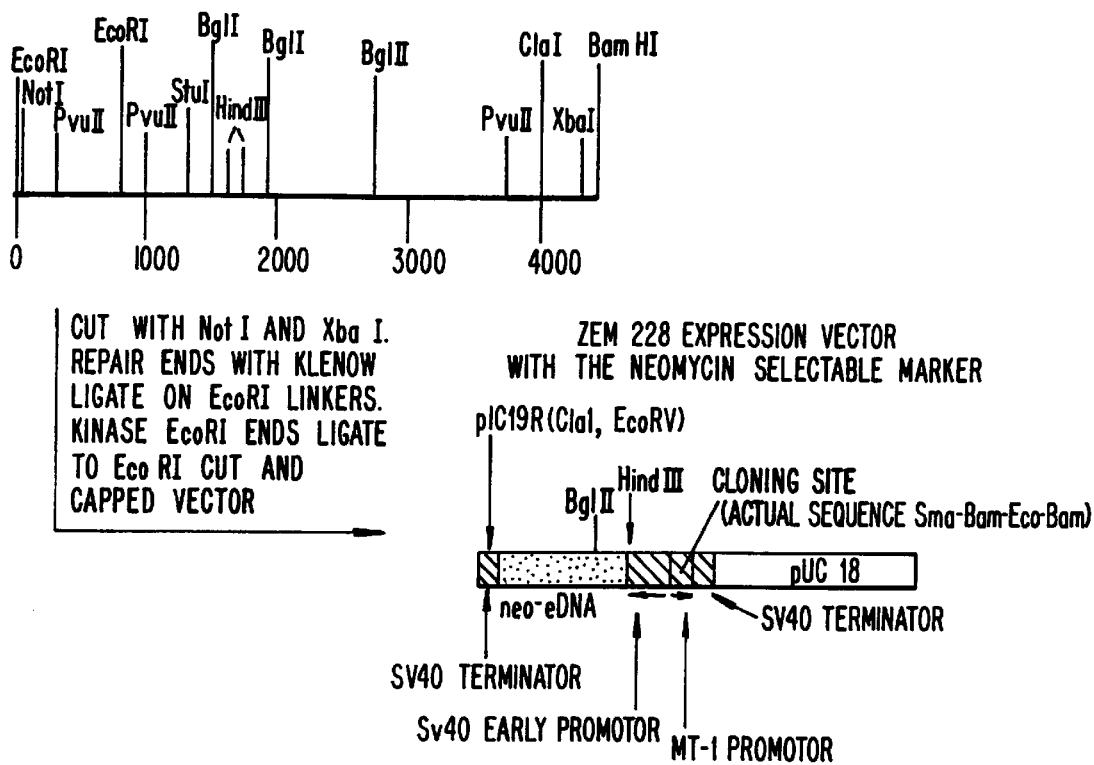
FIG. 4 illustrates the cloning of the receptor cDNA present in clone 45-A into Zem228R.

The entire $Glu_GR$ cDNA insert was removed from the pVEGT' cloning vector by digestion with Not I and Xba I. The ends were blunted with DNA polymerase I (Klenow fragment) and dNTPs, and were then ligated with Eco RI (Smart) linkers. After linker ligation, the insert with Eco RI ends in kinased and ligated to Eco RI-cut and capped Zem228 expression vector. Bacteria were transformed with the ligation reaction and clones were characterized by restriction analysis and partial sequencing (see FIG. 4).

Cultured mammalian cells, such as BHK 570 and BHK ts13 served as host cells for expression. Twenty-five μg of CsCl-purified DNA was precipitated with calcium phosphate and added to tissue culture cells in a 150 mm plate. After 4 hours the cells were subjected to a glycerol shock and were then put into non-selective medium. In some cases it may be necessary to include an antagonist to the $Glu_GR$ in the medium to prevent expression of a cytotoxic response in those cells where the $Glu_GR$ is expressed at levels high enough to cause a certain amount of autoactivation. Transiently expressed $Glu_GR$ ligand binding activity or PLC activation, cells are harvested after 48 hours. Stable expression was detected after 2 weeks of selection. The Zem228 expression vector includes a promoter capable of directing the transcription of the $Glu_GR$ gene, and a selectable marker for the bacterial neomycin resistance gene. Resistance to the drug G-418, an inhibitor of protein synthesis, was used to identify stably transfected clones. Presence of the SV40 ori region on the vector allows the expression construction to also be used for transient expression. In some instances it was preferable to include DNA for another selectable marker, the DHFR gene, in the transfection protocol. Selection with both G-418 and methotrexate allowed isolation of clones whose expression of $Glu_GR$ can be subsequently amplified by the addition of increasingly higher concentrations of methotrexate to the culture medium.

Transfected cell lines expressing $Glu_GR$ were identified by the binding of $^3$H-glutamate to membrane preparations from transfected cells. Cell lines expressing low to moderate levels of $Glu_GR$ are used to set up functional screening assays.

Clones of BHK 570 and BHK TK$^-$ts13 cells expressing the rat G protein coupled glutamate receptor cDNA were plated in two or three 150 mm maxi-plates culture dishes and were grown to confluency. The cells from each plate were scraped in 5 ml of PBS (phosphate buffered saline, Sigma Chemical Co., St. Louis, Mo.), which was was pre-chilled to 4° C. The cells were removed to a chilled centrifuged tube, and the plates were each rinsed with 5 ml of chilled PBS and pooled with the cells. The chilled tubes were spun at 1,000 rpm for two minutes, and the supernatant was discarded. The cells were frozen at either −70° C. or on dry ice. In some cases, the cells were left overnight at −70° C. The cells were thawed on ice and were resuspended in 10 ml of a buffer containing 30 mM Tris, pH 7.0, 2.5 mM $CaCl_2$, 1 mM PMSF, which was pre-chilled to 4° C., by homogenizing the cells for about 15 seconds. The suspension was poured into chilled centrifuge tubes. The homogenizer was rinsed with 10 ml of the same chilled solution, and the rinse was combined with the suspension. The centrifuge tubes were spun for fifteen minutes at 40,000×g at 4° C., and the supernatant was discarded. The pellet was homogenized with a buffer containing 30 mM Tris, pH 7.0, 2.5 mM $CaCl_2$, which was pre-chilled to 4° C. The homogenizer was rinsed with the chilled buffer, and the rinse was combined with the homogenate. The homogenate was spun as described above. The second homogenization was repeated on the resulting pellet. The final pellet was resuspended in between two and five milliliters of 30 mM Tris, pH 7.0, 2.5 mM $CaCl_2$, which was pre-chilled to 4° C. Triplicate samples were prepared for each plus and minus quisqualate assay point such that 250 μl aliquots of each homogenate sample were added to the wells of a 96-well microtiter plate. To a buffer containing 30 mM Tris, pH 7.0, 2.5 mM $CaCl_2$, which was pre-chilled to 4° C., a final concentration of 10 nM tritiated glutamic acid was added, and the solution was split in half. To one half, quisqualate was added to a final concentration of 1 mM. Two hundred and fifty microliter aliquots of either 30 mM Tris, pH 7.0, 2.5 mM $CaCl_2$, 5 nM tritiated glutamic acid and 500 mM quisqualate, or 30 mM Tris, pH 7.0, 2.5 mM $CaCl_2$, 5 nM tritiated glutamic acid were added to the triplicate samples. The samples were incubated for thirty minutes at room temperature. The samples were harvested onto glass filters and were immediately washed with ice-cold 30 mM Tris, pH 7.0, 2.5 mM $CaCl_2$ under vacuum using an LKB 1295-001 automated cell harvester (Pharmacia LKB, Piscataway, N.J.). The filters were dried in a microwave oven and counted in a gamma counter.

Protein determinations were carried out using a Coomassie Blue-based assay from Pierce Chemical Company (Rockford, Ill.) under conditions set forth by the manufacturer. One hundred microliters of undiluted cell homogenate or BSA standard was added to 2 ml of reagent and the optical density was measured at 595 nm. Protein concentrations of the samples were taken from a standard curve generated using the BSA standards diluted in 30 mM Tris, pH 7.0, 2.5 mM $CaCl_2$.

The results of these assays showed that quisqualate was able to competitively bind the glutamate receptor expressed by the transfected BHK cells.

Functional screening of agonists and antagonists

BHK 570 cells expressing GluGR or mock-transfected BHK 570 cells are plated into 24-well tissue culture dishes at about 100,000 cells per well. After 24 hours, the cells are labeled with 0.2 μCi of myo-(2-$^3$H) inositol (specific activity—20 Ci/mmol; New England Nuclear) per well. At the end of a 24 to 48 hour incubation, the cells are washed with prewarmed DMEM (Dulbecco's Modified Eagles Medium; Product No. 51-432, JRH Biosciences, Lenexa, Kans.) which has been buffered to pH 7.4 with Hepes buffer (Sigma Chemical Co.) containing 10 mM LiCl, and are incubated for five minutes at 37. The selected drugs are then added and the cells are incubated for an additional thirty minutes at 37° C. The reaction is stopped by placing the cells on ice, and the cells are lysed by aspirating off the media and adding 0.5 ml of cold DMEM and 0.5 ml of ice-cold 10% perchloric acid. After ten minutes the cell lysate is transferred to a tube on ice containing 250 μl 10 mM EDTA, pH 7.0. The samples are neutralized with 325 μl of 1.5M KOH in 60 mM Hepes Buffer. After the precipitates settles, 1.0 ml of the supernatant is applied to an Amprep minicolumn (Amersham, Arlington Heights, Ill., RPN1908). Inositol phosphates are eluted off the column and samples are counted in a scintillation counter. A positive response is indicated by an increase in labeled inositol phosphate levels.

What is claimed is:

1. An isolated mammalian G protein coupled glutamate receptor or a ligand binding fragment thereof, wherein the receptor has an amino acid sequence encoded by a DNA molecule that hybridizes at high stringency to an oligonucleotide of 60 or more contiguous nucleotides that is complementary to SEQ. ID. NO: 1.

2. The G protein coupled glutamate receptor of claim 1, which is substantially pure.

3. The G protein coupled glutamate receptor of claim 1, which is human or rodent.

4. The G protein coupled glutamate receptor of claim 1, which binds glutamate or quisqualate and thereby activates phospholipase C or stimulates inositol phospholipid metabolism in a vertebrate cell.

5. The composition of claim 1, wherein the isolated mammalian G protein coupled glutamate receptor or a fragment thereof is recombinantly produced.

6. An isolated mammalian G protein coupled glutamate receptor or a ligand binding fragment thereof, wherein the receptor is encoded by a DNA molecule that hybridizes at high stringency to a polynucleotide that is complementary to bases 2064 to 3624 of SEQ. ID. NO: 1.

* * * * *

UNITED STATES PATENT AND TRADEMARK OFFICE
CERTIFICATE OF CORRECTION

PATENT NO. : 5,869,609

DATED : February 9, 1999

INVENTOR(S) : Eileen Ranae Mulvihill, Frederick Stamner Hagen, Wolfhard Almers

It is certified that error appears in the above-identified patent and that said Letters Patent is hereby corrected as shown below:

On the title page, Item

[60] Division of Ser. No. 101,676, Aug. 3, 1993, abandoned, which is a continuation of 672,007, Mar. 18, 1991, abandoned, which is a continuation-in-part of 648,481, Jan. 30, 1991, abandoned, which is a continuation-in-part of 626,806, Dec. 12, 1990, abandoned.

Signed and Sealed this

Twelfth Day of December, 2000

*Attest:*

Q. TODD DICKINSON

*Attesting Officer*  *Director of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 4300 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Rattus norvegicus
        ( F ) TISSUE TYPE: Cerebellum ( v i i ) IMMEDIATE SOURCE:
        ( B ) CLONE: 45-A ( i x ) FEATURE:
        ( A ) NAME/KEY: CDS
        ( B ) LOCATION: 377..3973

( D ) OTHER INFORMATION:

( x i ) SEQUENCE DESCRIPTION: SEQ ID NO:1:

```
CCGAGAACGG  CTGCAGTCCT  CTGACCTGAG  ACCAATAGCT  GTGTCTACCC  GGACTCAGCG      60

TCCAGCTCAC  CGCCACTAAC  GCGCCGCGCA  TTGGACACCT  GATCCACACA  CCTTCGGGCA     120

CCAGTGAAAA  ACCGCGACTT  GATTTCTGG   AAGAACGCCC  CCAGGGTGTG  GGAGCGGTCG     180

TGGAGGACCA  GCAGGAGGAA  GCGGAGGGGA  GAGGGGCAGT  AGTGGAGGCA  GAGAAAGCGT     240

TGAACCAGCT  GTGTTGGCCG  AAGGCACGAA  ACGGCAAAAG  GCAGCGGTGA  GCATCTGTGT     300

GGTTCCCGCT  GGGAACCTGC  AGGCAGGACC  GGCGTGGGAA  CGTGGCTGGC  CCGCGGTGGA     360

CCGCGTCTTC  GCCACA ATG  GTC CGG CTC  CTC TTG ATT  TTC TTC CCA ATG          409
            Met Val Arg Leu Leu Leu Ile Phe Phe Pro Met
             1              5                       10
```

```
ATC TTT TTG GAG ATG TCC ATT TTG CCC AGG ATG CCT GAC AGA AAA GTA            457
Ile Phe Leu Glu Met Ser Ile Leu Pro Arg Met Pro Asp Arg Lys Val
             15                  20                  25
```

```
TTG CTG GCA GGT GCC TCG TCC CAG CGC TCC GTG GCG AGA ATG GAC GGA            505
Leu Leu Ala Gly Ala Ser Ser Gln Arg Ser Val Ala Arg Met Asp Gly
         30                  35                  40
```

```
GAT GTC ATC ATC GGA GCC CTC TTC TCA GTC CAT CAC CAG CCT CCA GCC            553
Asp Val Ile Ile Gly Ala Leu Phe Ser Val His His Gln Pro Pro Ala
         45                  50                  55
```

```
GAG AAG GTA CCC GAA AGG AAG TGT GGG GAG ATC AGG GAA CAG TAT GGT            601
Glu Lys Val Pro Glu Arg Lys Cys Gly Glu Ile Arg Glu Gln Tyr Gly
 60              65                  70                  75
```

```
ATC CAG AGG GTG GAG GCC ATG TTC CAC ACG TTG GAT AAG ATT AAC GCG            649
Ile Gln Arg Val Glu Ala Met Phe His Thr Leu Asp Lys Ile Asn Ala
                 80                  85                  90
```

```
GAC CCG GTG CTC CTG CCC AAC ATC ACT CTG GGC AGT GAG ATC CGG GAC            697
Asp Pro Val Leu Leu Pro Asn Ile Thr Leu Gly Ser Glu Ile Arg Asp
                 95                 100                 105
```

```
TCC TGC TGG CAC TCT TCA GTG GCT CTC GAA CAG AGC ATC GAA TTC ATC            745
Ser Cys Trp His Ser Ser Val Ala Leu Glu Gln Ser Ile Glu Phe Ile
                110                 115                 120
```

```
AGA GAC TCC CTG ATT TCC ATC CGA GAT GAG AAG GAT GGG CTG AAC CGA            793
Arg Asp Ser Leu Ile Ser Ile Arg Asp Glu Lys Asp Gly Leu Asn Arg
125                 130                 135
```

```
TGC CTG CCT GAT GGC CAG ACC CTG CCC CCT GGC AGG ACT AAG AAG CCT            841
Cys Leu Pro Asp Gly Gln Thr Leu Pro Pro Gly Arg Thr Lys Lys Pro
140                 145                 150                 155
```

```
ATT GCT GGA GTG ATC GGC CCT GGC TCC AGC TCT GTG GCC ATT CAA GTC            889
Ile Ala Gly Val Ile Gly Pro Gly Ser Ser Ser Val Ala Ile Gln Val
                160                 165                 170
```

```
CAG AAT CTT CTC CAG CTG TTC GAC ATC CCA CAG ATC GCC TAT TCT GCC            937
Gln Asn Leu Leu Gln Leu Phe Asp Ile Pro Gln Ile Ala Tyr Ser Ala
                175                 180                 185
```

```
ACA AGC ATA GAC CTG AGT GAC AAA ACT TTG TAC AAA TAC TTC CTG AGG            985
Thr Ser Ile Asp Leu Ser Asp Lys Thr Leu Tyr Lys Tyr Phe Leu Arg
                190                 195                 200
```

```
GTG GTC CCT TCT GAC ACT TTG CAG GCA AGG GCG ATG CTC GAC ATA GTC           1033
Val Val Pro Ser Asp Thr Leu Gln Ala Arg Ala Met Leu Asp Ile Val
205                 210                 215
```

```
AAG CGT TAC AAC TGG ACC TAT GTC TCA GCA GTC CAC ACA GAA GGG AAT           1081
Lys Arg Tyr Asn Trp Thr Tyr Val Ser Ala Val His Thr Glu Gly Asn
220                 225                 230                 235
```

```
TAC GGC GAG AGT GGA ATG GAT GCT TTC AAA GAA CTG GCT GCC CAG GAA           1129
Tyr Gly Glu Ser Gly Met Asp Ala Phe Lys Glu Leu Ala Ala Gln Glu
                240                 245                 250
```

```
GGC CTC TGC ATC GCA CAC TCG GAC AAA ATC TAC AGC AAT GCT GGC GAG    1177
Gly Leu Cys Ile Ala His Ser Asp Lys Ile Tyr Ser Asn Ala Gly Glu
            255             260             265

AAG AGC TTT GAC CGG CTC CTG CGT AAA CTC CGG GAG CGG CTT CCC AAG    1225
Lys Ser Phe Asp Arg Leu Leu Arg Lys Leu Arg Glu Arg Leu Pro Lys
        270             275             280

GCC AGG GTT GTG GTC TGC TTC TGC GAG GGC ATG ACA GTG CGG GGC TTA    1273
Ala Arg Val Val Val Cys Phe Cys Glu Gly Met Thr Val Arg Gly Leu
    285             290             295

CTG AGT GCC ATG CGC CGC CTG GGC GTC GTG GGC GAG TTC TCA CTC ATT    1321
Leu Ser Ala Met Arg Arg Leu Gly Val Val Gly Glu Phe Ser Leu Ile
300             305             310             315

GGA AGT GAT GGA TGG GCA GAC AGA GAT GAA GTC ATC GAA GGC TAT GAG    1369
Gly Ser Asp Gly Trp Ala Asp Arg Asp Glu Val Ile Glu Gly Tyr Glu
                320             325             330

GTG GAA GCC AAC GGA GGG ATC ACA ATA AAG CTT CAG TCT CCA GAG GTC    1417
Val Glu Ala Asn Gly Gly Ile Thr Ile Lys Leu Gln Ser Pro Glu Val
335             340             345

AGG TCA TTT GAT GAC TAC TTC CTG AAG CTG AGG CTG GAC ACC AAC ACA    1465
Arg Ser Phe Asp Asp Tyr Phe Leu Lys Leu Arg Leu Asp Thr Asn Thr
        350             355             360

AGG AAT CCT TGG TTC CCT GAG TTC TGG CAA CAT CGC TTC CAG TGT CGC    1513
Arg Asn Pro Trp Phe Pro Glu Phe Trp Gln His Arg Phe Gln Cys Arg
    365             370             375

CTA CCT GGA CAC CTC TTG GAA AAC CCC AAC TTT AAG AAA GTG TGC ACA    1561
Leu Pro Gly His Leu Leu Glu Asn Pro Asn Phe Lys Lys Val Cys Thr
380             385             390             395

GGA AAT GAA AGC TTG GAA GAA AAC TAT GTC CAG GAC AGC AAA ATG GGA    1609
Gly Asn Glu Ser Leu Glu Glu Asn Tyr Val Gln Asp Ser Lys Met Gly
                400             405             410

TTT GTC ATC AAT GCC ATC TAT GCC ATG GCA CAT GGG CTG CAG AAC ATG    1657
Phe Val Ile Asn Ala Ile Tyr Ala Met Ala His Gly Leu Gln Asn Met
415             420             425

CAC CAT GCT CTG TGT CCC GGC CAT GTG GGC CTG TGT GAT GCT ATG AAA    1705
His His Ala Leu Cys Pro Gly His Val Gly Leu Cys Asp Ala Met Lys
        430             435             440

CCC ATT GAT GGC AGG AAG CTC CTG GAT TTC CTC ATC AAA TCC TCT TTT    1753
Pro Ile Asp Gly Arg Lys Leu Leu Asp Phe Leu Ile Lys Ser Ser Phe
    445             450             455

GTC GGA GTG TCT GGA GAG GAG GTG TGG TTC GAT GAG AAG GGG GAT GCT    1801
Val Gly Val Ser Gly Glu Glu Val Trp Phe Asp Glu Lys Gly Asp Ala
460             465             470             475

CCC GGA AGG TAT GAC ATT ATG AAT CTG CAG TAC ACA GAA GCT AAT CGC    1849
Pro Gly Arg Tyr Asp Ile Met Asn Leu Gln Tyr Thr Glu Ala Asn Arg
                480             485             490

TAT GAC TAT GTC CAC GTG GGG ACC TGG CAT GAA GGA GTG CTG AAT ATT    1897
Tyr Asp Tyr Val His Val Gly Thr Trp His Glu Gly Val Leu Asn Ile
            495             500             505

GAT GAT TAC AAA ATC CAG ATG AAC AAA AGC GGA ATG GTA CGA TCT GTG    1945
Asp Asp Tyr Lys Ile Gln Met Asn Lys Ser Gly Met Val Arg Ser Val
        510             515             520

TGC AGT GAG CCT TGC TTA AAG GGT CAG ATT AAG GTC ATA CGG AAA GGA    1993
Cys Ser Glu Pro Cys Leu Lys Gly Gln Ile Lys Val Ile Arg Lys Gly
525             530             535

GAA GTG AGC TGC TGC TGG ATC TGC ACG GCC TGC AAA GAG AAT GAG TTT    2041
Glu Val Ser Cys Cys Trp Ile Cys Thr Ala Cys Lys Glu Asn Glu Phe
540             545             550             555

GTG CAG GAC GAG TTC ACC TGC AGA GCC TGT GAC CTG GGG TGG TGG CCC    2089
Val Gln Asp Glu Phe Thr Cys Arg Ala Cys Asp Leu Gly Trp Trp Pro
                560             565             570
```

| | | | | | | | | | | | | | | | | |
|---|---|---|---|---|---|---|---|---|---|---|---|---|---|---|---|---|
| AAC | GCA | GAG | CTC | ACA | GGC | TGT | GAG | CCC | ATT | CCT | GTC | CGT | TAT | CTT | GAG | 2137 |
| Asn | Ala | Glu | Leu | Thr | Gly | Cys | Glu | Pro | Ile | Pro | Val | Arg | Tyr | Leu | Glu | |
| | | | | 575 | | | | 580 | | | | | 585 | | | |
| TGG | AGT | GAC | ATA | GAA | TCT | ATC | ATA | GCC | ATC | GCC | TTT | TCT | TGC | CTG | GGC | 2185 |
| Trp | Ser | Asp | Ile | Glu | Ser | Ile | Ile | Ala | Ile | Ala | Phe | Ser | Cys | Leu | Gly | |
| | | | | 590 | | | | 595 | | | | | 600 | | | |
| ATC | CTC | GTG | ACG | CTG | TTT | GTC | ACC | CTC | ATC | TTC | GTT | CTG | TAC | CGG | GAC | 2233 |
| Ile | Leu | Val | Thr | Leu | Phe | Val | Thr | Leu | Ile | Phe | Val | Leu | Tyr | Arg | Asp | |
| | | 605 | | | | 610 | | | | | 615 | | | | | |
| ACA | CCC | GTG | GTC | AAA | TCC | TCC | AGT | AGG | GAG | CTC | TGC | TAT | ATC | ATT | CTG | 2281 |
| Thr | Pro | Val | Val | Lys | Ser | Ser | Ser | Arg | Glu | Leu | Cys | Tyr | Ile | Ile | Leu | |
| 620 | | | | | 625 | | | | 630 | | | | | | 635 | |
| GCT | GGT | ATT | TTC | CTC | GGC | TAT | GTG | TGC | CCT | TTC | ACC | CTC | ATC | GCC | AAA | 2329 |
| Ala | Gly | Ile | Phe | Leu | Gly | Tyr | Val | Cys | Pro | Phe | Thr | Leu | Ile | Ala | Lys | |
| | | | | 640 | | | | 645 | | | | | 650 | | | |
| CCT | ACT | ACC | ACA | TCC | TGC | TAC | CTC | CAG | CGC | CTC | CTA | GTT | GGC | CTC | TCT | 2377 |
| Pro | Thr | Thr | Thr | Ser | Cys | Tyr | Leu | Gln | Arg | Leu | Leu | Val | Gly | Leu | Ser | |
| | | | 655 | | | | 660 | | | | | 665 | | | | |
| TCT | GCC | ATG | TGC | TAC | TCT | GCT | TTA | GTG | ACC | AAA | ACC | AAT | CGT | ATT | GCA | 2425 |
| Ser | Ala | Met | Cys | Tyr | Ser | Ala | Leu | Val | Thr | Lys | Thr | Asn | Arg | Ile | Ala | |
| | | 670 | | | | 675 | | | | | 680 | | | | | |
| CGC | ATC | CTG | GCT | GGC | AGC | AAG | AAG | AAG | ATC | TGC | ACC | CGG | AAG | CCC | AGA | 2473 |
| Arg | Ile | Leu | Ala | Gly | Ser | Lys | Lys | Lys | Ile | Cys | Thr | Arg | Lys | Pro | Arg | |
| | 685 | | | | 690 | | | | | 695 | | | | | | |
| TTC | ATG | AGC | GCT | TGG | GCC | CAA | GTG | ATC | ATA | GCC | TCC | ATT | CTG | ATT | AGT | 2521 |
| Phe | Met | Ser | Ala | Trp | Ala | Gln | Val | Ile | Ile | Ala | Ser | Ile | Leu | Ile | Ser | |
| 700 | | | | | 705 | | | | | 710 | | | | | 715 | |
| GTA | CAG | CTA | ACA | CTA | GTG | GTG | ACC | TTG | ATC | ATC | ATG | GAG | CCT | CCC | ATG | 2569 |
| Val | Gln | Leu | Thr | Leu | Val | Val | Thr | Leu | Ile | Ile | Met | Glu | Pro | Pro | Met | |
| | | | | 720 | | | | 725 | | | | | 730 | | | |
| CCC | ATT | TTG | TCC | TAC | CCG | AGT | ATC | AAG | GAA | GTC | TAC | CTT | ATC | TGC | AAT | 2617 |
| Pro | Ile | Leu | Ser | Tyr | Pro | Ser | Ile | Lys | Glu | Val | Tyr | Leu | Ile | Cys | Asn | |
| | | | 735 | | | | 740 | | | | | 745 | | | | |
| ACC | AGC | AAC | CTG | GGT | GTA | GTG | GCC | CCT | GTG | GGT | TAC | AAT | GGA | CTC | CTC | 2665 |
| Thr | Ser | Asn | Leu | Gly | Val | Val | Ala | Pro | Val | Gly | Tyr | Asn | Gly | Leu | Leu | |
| | | 750 | | | | 755 | | | | | 760 | | | | | |
| ATC | ATG | AGC | TGT | ACC | TAC | TAT | GCC | TTC | AAG | ACC | CGC | AAC | GTG | CCG | GCC | 2713 |
| Ile | Met | Ser | Cys | Thr | Tyr | Tyr | Ala | Phe | Lys | Thr | Arg | Asn | Val | Pro | Ala | |
| | 765 | | | | 770 | | | | | 775 | | | | | | |
| AAC | TTC | AAT | GAG | GCT | AAA | TAC | ATC | GCC | TTC | ACC | ATG | TAC | ACT | ACC | TGC | 2761 |
| Asn | Phe | Asn | Glu | Ala | Lys | Tyr | Ile | Ala | Phe | Thr | Met | Tyr | Thr | Thr | Cys | |
| 780 | | | | | 785 | | | | | 790 | | | | | 795 | |
| ATC | ATC | TGG | CTG | GCT | TTC | GTT | CCC | ATT | TAC | TTT | GGG | AGC | AAC | TAC | AAG | 2809 |
| Ile | Ile | Trp | Leu | Ala | Phe | Val | Pro | Ile | Tyr | Phe | Gly | Ser | Asn | Tyr | Lys | |
| | | | | 800 | | | | 805 | | | | | 810 | | | |
| ATC | ATC | ACT | ACC | TGC | TTC | GCG | GTG | AGC | CTC | AGT | GTG | ACG | GTG | GCC | CTG | 2857 |
| Ile | Ile | Thr | Thr | Cys | Phe | Ala | Val | Ser | Leu | Ser | Val | Thr | Val | Ala | Leu | |
| | | | 815 | | | | 820 | | | | | 825 | | | | |
| GGG | TGC | ATG | TTT | ACT | CCG | AAG | ATG | TAC | ATC | ATC | ATT | GCC | AAA | CCT | GAG | 2905 |
| Gly | Cys | Met | Phe | Thr | Pro | Lys | Met | Tyr | Ile | Ile | Ile | Ala | Lys | Pro | Glu | |
| | | 830 | | | | 835 | | | | | 840 | | | | | |
| AGG | AAC | GTC | CGC | AGT | GCC | TTC | ACG | ACC | TCT | GAT | GTT | GTC | CGC | ATG | CAC | 2953 |
| Arg | Asn | Val | Arg | Ser | Ala | Phe | Thr | Thr | Ser | Asp | Val | Val | Arg | Met | His | |
| | | 845 | | | | 850 | | | | | 855 | | | | | |
| GTC | GGT | GAT | GGC | AAA | CTG | CCG | TGC | CGC | TCC | AAC | ACC | TTC | CTC | AAC | ATT | 3001 |
| Val | Gly | Asp | Gly | Lys | Leu | Pro | Cys | Arg | Ser | Asn | Thr | Phe | Leu | Asn | Ile | |
| 860 | | | | | 865 | | | | | 870 | | | | | 875 | |
| TTC | CGG | AGA | AAG | AAG | CCC | GGG | GCA | GGG | AAT | GCC | AAT | TCT | AAC | GGC | AAG | 3049 |
| Phe | Arg | Arg | Lys | Lys | Pro | Gly | Ala | Gly | Asn | Ala | Asn | Ser | Asn | Gly | Lys | |
| | | | 880 | | | | 885 | | | | | 890 | | | | |

| | | | | | | | | | | | | | | | | |
|---|---|---|---|---|---|---|---|---|---|---|---|---|---|---|---|---|
| TCT | GTG | TCA | TGG | TCT | GAA | CCA | GGT | GGA | AGA | CAG | GCG | CCC | AAG | GGA | CAG | 3097 |
| Ser | Val | Ser | Trp 895 | Ser | Glu | Pro | Gly 900 | Gly | Arg | Gln | Ala | Pro 905 | Lys | Gly | Gln | |
| CAC | GTG | TGG | CAG | CGC | CTC | TCT | GTG | CAC | GTG | AAG | ACC | AAC | GAG | ACG | GCC | 3145 |
| His | Val | Trp 910 | Gln | Arg | Leu | Ser | Val 915 | His | Val | Lys | Thr | Asn 920 | Glu | Thr | Ala | |
| TGT | AAC | CAA | ACA | GCC | GTA | ATC | AAA | CCC | CTC | ACT | AAA | AGT | TAC | CAA | GGC | 3193 |
| Cys | Asn 925 | Gln | Thr | Ala | Val | Ile | Lys 930 | Pro | Leu | Thr | Lys | Ser 935 | Tyr | Gln | Gly | |
| TCT | GGC | AAG | AGC | CTG | ACC | TTT | TCA | GAT | GCC | AGC | ACC | AAG | ACC | CTT | TAC | 3241 |
| Ser 940 | Gly | Lys | Ser | Leu | Thr 945 | Phe | Ser | Asp | Ala | Ser 950 | Thr | Lys | Thr | Leu | Tyr 955 | |
| AAT | GTG | GAA | GAA | GAG | GAC | AAT | ACC | CCT | TCT | GCT | CAC | TTC | AGC | CCT | CCC | 3289 |
| Asn | Val | Glu | Glu | Glu 960 | Asp | Asn | Thr | Pro | Ser 965 | Ala | His | Phe | Ser | Pro 970 | Pro | |
| AGC | AGC | CCT | TCT | ATG | GTG | GTG | CAC | CGA | CGC | GGG | CCA | CCC | GTG | GCC | ACC | 3337 |
| Ser | Ser | Pro | Ser 975 | Met | Val | Val | His | Arg 980 | Arg | Gly | Pro | Pro | Val 985 | Ala | Thr | |
| ACA | CCA | CCT | CTG | CCA | CCC | CAT | CTG | ACC | GCA | GAA | GAG | ACC | CCC | CTG | TTC | 3385 |
| Thr | Pro | Pro 990 | Leu | Pro | Pro | His | Leu 995 | Thr | Ala | Glu | Glu | Thr 1000 | Pro | Leu | Phe | |
| CTG | GCT | GAT | TCC | GTC | ATC | CCC | AAG | GGC | TTG | CCT | CCT | CCT | CTC | CCG | CAG | 3433 |
| Leu | Ala | Asp 1005 | Ser | Val | Ile | Pro | Lys 1010 | Gly | Leu | Pro | Pro | Pro 1015 | Leu | Pro | Gln | |
| CAG | CAG | CCA | CAG | CAG | CCG | CCC | CCT | CAG | CAG | CCC | CCG | CAG | CAG | CCC | AAG | 3481 |
| Gln 1020 | Gln | Pro | Gln | Gln | Pro 1025 | Pro | Pro | Gln | Gln | Pro 1030 | Pro | Gln | Gln | Pro | Lys 1035 | |
| TCC | CTG | ATG | GAC | CAG | CTG | CAA | GGC | GTA | GTC | ACC | AAC | TTC | GGT | TCG | GGG | 3529 |
| Ser | Leu | Met | Asp | Gln 1040 | Leu | Gln | Gly | Val | Val 1045 | Thr | Asn | Phe | Gly | Ser 1050 | Gly | |
| ATT | CCA | GAT | TTC | CAT | GCG | GTG | CTG | GCA | GGC | CCG | GGG | ACA | CCA | GGA | AAC | 3577 |
| Ile | Pro | Asp | Phe | His 1055 | Ala | Val | Leu | Ala | Gly 1060 | Pro | Gly | Thr | Pro | Gly 1065 | Asn | |
| AGC | CTG | CGC | TCT | CTG | TAC | CCG | CCC | CCG | CCT | CCG | CAA | CAC | CTG | CAG | | 3625 |
| Ser | Leu | Arg | Ser 1070 | Leu | Tyr | Pro | Pro | Pro 1075 | Pro | Pro | Gln | His | Leu 1080 | Gln | | |
| ATG | CTG | CCC | CTG | CAC | CTG | AGC | ACC | TTC | CAG | GAG | GAG | TCC | ATC | TCC | CCT | 3673 |
| Met | Leu | Pro 1085 | Leu | His | Leu | Ser | Thr 1090 | Phe | Gln | Glu | Glu | Ser 1095 | Ile | Ser | Pro | |
| CCT | GGG | GAG | GAC | ATC | GAT | GAT | GAC | AGT | GAG | AGA | TTC | AAG | CTC | CTG | CAG | 3721 |
| Pro 1100 | Gly | Glu | Asp | Ile | Asp 1105 | Asp | Asp | Ser | Glu | Arg 1110 | Phe | Lys | Leu | Leu | Gln 1115 | |
| GAG | TTC | GTG | TAC | GAG | CGC | GAA | GGG | AAC | ACC | GAA | GAA | GAT | GAA | TTG | GAA | 3769 |
| Glu | Phe | Val | Tyr | Glu 1120 | Arg | Glu | Gly | Asn | Thr 1125 | Glu | Glu | Asp | Glu | Leu 1130 | Glu | |
| GAG | GAG | GAG | GAC | CTG | CCC | ACA | GCC | AGC | AAG | CTG | ACC | CCT | GAG | GAT | TCT | 3817 |
| Glu | Glu | Glu | Asp 1135 | Leu | Pro | Thr | Ala | Ser 1140 | Lys | Leu | Thr | Pro | Glu 1145 | Asp | Ser | |
| CCT | GCC | CTG | ACG | CCT | CCT | TCT | CCT | TTC | CGA | GAT | TCC | GTG | GCC | TCT | GGC | 3865 |
| Pro | Ala | Leu | Thr 1150 | Pro | Pro | Ser | Pro | Phe 1155 | Arg | Asp | Ser | Val | Ala 1160 | Ser | Gly | |
| AGC | TCA | GTG | CCC | AGT | TCC | CCC | GTA | TCT | GAG | TCG | GTC | CTC | TGC | ACC | CCT | 3913 |
| Ser | Ser | Val | Pro | Ser 1165 | Ser | Pro | Val | Ser | Glu 1170 | Ser | Val | Leu | Cys | Thr 1175 | Pro | |
| CCA | AAT | GTA | ACC | TAC | GCC | TCT | GTC | ATT | CTG | AGG | GAC | TAC | AAG | CAA | AGC | 3961 |
| Pro | Asn | Val | Thr 1180 | Tyr | Ala | Ser | Val | Ile 1185 | Leu | Arg | Asp | Tyr | Lys 1190 | Gln | Ser 1195 | |
| TCT | TCC | ACC | CTG | TAGTGTGTGT | GTGTGTGTGG | GGGCGGGGGG | AGTGCGCATG | | | | | | | | | 4013 |
| Ser | Ser | Thr | Leu | | | | | | | | | | | | | |
| GAGAAGCCAG | AGATGCCAAG | GAGTGTCAAC | CCTTCCAGAA | ATGTGTAGAA | AGCAGGGTGA | | | | | | | | | | | 4073 |

```
GGGATGGGGA  TGGAGGACCA  CGGTCTGCAG  GGAAGAAAAA  AAAAATGCTG  CGGCTGCCTT    4133

AAAGAAGGAG  AGGGACGATG  CCAACTGAAC  AGTGGTCCTG  GCCAGGATTG  TGACTCTTGA    4193

ATTATTCAAA  AACCTTCTCT  AGAAAGAAAG  GGAATTATGA  CAAAGCACAA  TTCCATATGG    4253

TATGTAACTT  TTATCGAAAA  AAAAAAAAAA  AAAAAAAAAA  AAAAAA                    4300
```

( 2 ) INFORMATION FOR SEQ ID NO:2:

( i ) SEQUENCE CHARACTERISTICS:
        ( A ) LENGTH: 1199 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Val  Arg  Leu  Leu  Leu  Ile  Phe  Phe  Pro  Met  Ile  Phe  Leu  Glu  Met
  1                  5                      10                      15

Ser  Ile  Leu  Pro  Arg  Met  Pro  Asp  Arg  Lys  Val  Leu  Leu  Ala  Gly  Ala
                20                      25                      30

Ser  Ser  Gln  Arg  Ser  Val  Ala  Arg  Met  Asp  Gly  Asp  Val  Ile  Ile  Gly
            35                      40                      45

Ala  Leu  Phe  Ser  Val  His  His  Gln  Pro  Pro  Ala  Glu  Lys  Val  Pro  Glu
        50                      55                      60

Arg  Lys  Cys  Gly  Glu  Ile  Arg  Glu  Gln  Tyr  Gly  Ile  Gln  Arg  Val  Glu
 65                      70                      75                      80

Ala  Met  Phe  His  Thr  Leu  Asp  Lys  Ile  Asn  Ala  Asp  Pro  Val  Leu  Leu
                    85                      90                      95

Pro  Asn  Ile  Thr  Leu  Gly  Ser  Glu  Ile  Arg  Asp  Ser  Cys  Trp  His  Ser
              100                     105                     110

Ser  Val  Ala  Leu  Glu  Gln  Ser  Ile  Glu  Phe  Ile  Arg  Asp  Ser  Leu  Ile
          115                     120                     125

Ser  Ile  Arg  Asp  Glu  Lys  Asp  Gly  Leu  Asn  Arg  Cys  Leu  Pro  Asp  Gly
     130                     135                     140

Gln  Thr  Leu  Pro  Pro  Gly  Arg  Thr  Lys  Lys  Pro  Ile  Ala  Gly  Val  Ile
145                     150                     155                     160

Gly  Pro  Gly  Ser  Ser  Ser  Val  Ala  Ile  Gln  Val  Gln  Asn  Leu  Leu  Gln
                  165                     170                     175

Leu  Phe  Asp  Ile  Pro  Gln  Ile  Ala  Tyr  Ser  Ala  Thr  Ser  Ile  Asp  Leu
              180                     185                     190

Ser  Asp  Lys  Thr  Leu  Tyr  Lys  Tyr  Phe  Leu  Arg  Val  Val  Pro  Ser  Asp
          195                     200                     205

Thr  Leu  Gln  Ala  Arg  Ala  Met  Leu  Asp  Ile  Val  Lys  Arg  Tyr  Asn  Trp
     210                     215                     220

Thr  Tyr  Val  Ser  Ala  Val  His  Thr  Glu  Gly  Asn  Tyr  Gly  Glu  Ser  Gly
225                     230                     235                     240

Met  Asp  Ala  Phe  Lys  Glu  Leu  Ala  Ala  Gln  Glu  Gly  Leu  Cys  Ile  Ala
                  245                     250                     255

His  Ser  Asp  Lys  Ile  Tyr  Ser  Asn  Ala  Gly  Glu  Lys  Ser  Phe  Asp  Arg
              260                     265                     270

Leu  Leu  Arg  Lys  Leu  Arg  Glu  Arg  Leu  Pro  Lys  Ala  Arg  Val  Val  Val
          275                     280                     285

Cys  Phe  Cys  Glu  Gly  Met  Thr  Val  Arg  Gly  Leu  Leu  Ser  Ala  Met  Arg
     290                     295                     300

Arg  Leu  Gly  Val  Val  Gly  Glu  Phe  Ser  Leu  Ile  Gly  Ser  Asp  Gly  Trp
305                     310                     315                     320
```

-continued

| | | | | | | | | | | | | | | |
|---|---|---|---|---|---|---|---|---|---|---|---|---|---|---|
| Ala | Asp | Arg | Asp | Glu | Val | Ile | Glu | Gly | Tyr | Glu | Val | Glu | Ala | Asn | Gly |
| | | | 325 | | | | | 330 | | | | | 335 | |
| Gly | Ile | Thr | Ile | Lys | Leu | Gln | Ser | Pro | Glu | Val | Arg | Ser | Phe | Asp | Asp |
| | | | 340 | | | | 345 | | | | | 350 | | | |
| Tyr | Phe | Leu | Lys | Leu | Arg | Leu | Asp | Thr | Asn | Thr | Arg | Asn | Pro | Trp | Phe |
| | | 355 | | | | 360 | | | | | 365 | | | | |
| Pro | Glu | Phe | Trp | Gln | His | Arg | Phe | Gln | Cys | Arg | Leu | Pro | Gly | His | Leu |
| | 370 | | | | 375 | | | | | 380 | | | | | |
| Leu | Glu | Asn | Pro | Asn | Phe | Lys | Lys | Val | Cys | Thr | Gly | Asn | Glu | Ser | Leu |
| 385 | | | | 390 | | | | 395 | | | | | | 400 | |
| Glu | Glu | Asn | Tyr | Val | Gln | Asp | Ser | Lys | Met | Gly | Phe | Val | Ile | Asn | Ala |
| | | | 405 | | | | | 410 | | | | | 415 | | |
| Ile | Tyr | Ala | Met | Ala | His | Gly | Leu | Gln | Asn | Met | His | His | Ala | Leu | Cys |
| | | | 420 | | | | | 425 | | | | | 430 | | |
| Pro | Gly | His | Val | Gly | Leu | Cys | Asp | Ala | Met | Lys | Pro | Ile | Asp | Gly | Arg |
| | | 435 | | | | | 440 | | | | | 445 | | | |
| Lys | Leu | Leu | Asp | Phe | Leu | Ile | Lys | Ser | Ser | Phe | Val | Gly | Val | Ser | Gly |
| | | 450 | | | | 455 | | | | | 460 | | | | |
| Glu | Glu | Val | Trp | Phe | Asp | Glu | Lys | Gly | Asp | Ala | Pro | Gly | Arg | Tyr | Asp |
| 465 | | | | | 470 | | | | 475 | | | | | | 480 |
| Ile | Met | Asn | Leu | Gln | Tyr | Thr | Glu | Ala | Asn | Arg | Tyr | Asp | Tyr | Val | His |
| | | | | 485 | | | | | 490 | | | | | 495 | |
| Val | Gly | Thr | Trp | His | Glu | Gly | Val | Leu | Asn | Ile | Asp | Asp | Tyr | Lys | Ile |
| | | | | 500 | | | | | 505 | | | | | 510 | |
| Gln | Met | Asn | Lys | Ser | Gly | Met | Val | Arg | Ser | Val | Cys | Ser | Glu | Pro | Cys |
| | | | 515 | | | | 520 | | | | | 525 | | | |
| Leu | Lys | Gly | Gln | Ile | Lys | Val | Ile | Arg | Lys | Gly | Glu | Val | Ser | Cys | Cys |
| | 530 | | | | | 535 | | | | | 540 | | | | |
| Trp | Ile | Cys | Thr | Ala | Cys | Lys | Glu | Asn | Glu | Phe | Val | Gln | Asp | Glu | Phe |
| 545 | | | | | 550 | | | | | 555 | | | | | 560 |
| Thr | Cys | Arg | Ala | Cys | Asp | Leu | Gly | Trp | Trp | Pro | Asn | Ala | Glu | Leu | Thr |
| | | | | 565 | | | | | 570 | | | | | 575 | |
| Gly | Cys | Glu | Pro | Ile | Pro | Val | Arg | Tyr | Leu | Glu | Trp | Ser | Asp | Ile | Glu |
| | | | 580 | | | | | 585 | | | | | 590 | | |
| Ser | Ile | Ile | Ala | Ile | Ala | Phe | Ser | Cys | Leu | Gly | Ile | Leu | Val | Thr | Leu |
| | | 595 | | | | | 600 | | | | | 605 | | | |
| Phe | Val | Thr | Leu | Ile | Phe | Val | Leu | Tyr | Arg | Asp | Thr | Pro | Val | Val | Lys |
| | | 610 | | | | 615 | | | | | 620 | | | | |
| Ser | Ser | Ser | Arg | Glu | Leu | Cys | Tyr | Ile | Ile | Leu | Ala | Gly | Ile | Phe | Leu |
| 625 | | | | | 630 | | | | | 635 | | | | | 640 |
| Gly | Tyr | Val | Cys | Pro | Phe | Thr | Leu | Ile | Ala | Lys | Pro | Thr | Thr | Thr | Ser |
| | | | | 645 | | | | | 650 | | | | | 655 | |
| Cys | Tyr | Leu | Gln | Arg | Leu | Leu | Val | Gly | Leu | Ser | Ser | Ala | Met | Cys | Tyr |
| | | | 660 | | | | | 665 | | | | | 670 | | |
| Ser | Ala | Leu | Val | Thr | Lys | Thr | Asn | Arg | Ile | Ala | Arg | Ile | Leu | Ala | Gly |
| | | | 675 | | | | | 680 | | | | | 685 | | |
| Ser | Lys | Lys | Lys | Ile | Cys | Thr | Arg | Lys | Pro | Arg | Phe | Met | Ser | Ala | Trp |
| | | 690 | | | | | 695 | | | | | 700 | | | |
| Ala | Gln | Val | Ile | Ile | Ala | Ser | Ile | Leu | Ile | Ser | Val | Gln | Leu | Thr | Leu |
| 705 | | | | | 710 | | | | | 715 | | | | | 720 |
| Val | Val | Thr | Leu | Ile | Ile | Met | Glu | Pro | Pro | Met | Pro | Ile | Leu | Ser | Tyr |
| | | | | 725 | | | | | 730 | | | | | 735 | |
| Pro | Ser | Ile | Lys | Glu | Val | Tyr | Leu | Ile | Cys | Asn | Thr | Ser | Asn | Leu | Gly |

```
                        740                     745                      750
Val  Val  Ala  Pro  Val  Gly  Tyr  Asn  Gly  Leu  Leu  Ile  Met  Ser  Cys  Thr
               755                     760                     765

Tyr  Tyr  Ala  Phe  Lys  Thr  Arg  Asn  Val  Pro  Ala  Asn  Phe  Asn  Glu  Ala
770                     775                     780

Lys  Tyr  Ile  Ala  Phe  Thr  Met  Tyr  Thr  Thr  Cys  Ile  Ile  Trp  Leu  Ala
785                     790                     795                          800

Phe  Val  Pro  Ile  Tyr  Phe  Gly  Ser  Asn  Tyr  Lys  Ile  Ile  Thr  Thr  Cys
                    805                     810                     815

Phe  Ala  Val  Ser  Leu  Ser  Val  Thr  Val  Ala  Leu  Gly  Cys  Met  Phe  Thr
               820                     825                     830

Pro  Lys  Met  Tyr  Ile  Ile  Ile  Ala  Lys  Pro  Glu  Arg  Asn  Val  Arg  Ser
               835                     840                     845

Ala  Phe  Thr  Thr  Ser  Asp  Val  Val  Arg  Met  His  Val  Gly  Asp  Gly  Lys
850                     855                     860

Leu  Pro  Cys  Arg  Ser  Asn  Thr  Phe  Leu  Asn  Ile  Phe  Arg  Arg  Lys  Lys
865                     870                     875                          880

Pro  Gly  Ala  Gly  Asn  Ala  Asn  Ser  Asn  Gly  Lys  Ser  Val  Ser  Trp  Ser
                    885                     890                     895

Glu  Pro  Gly  Gly  Arg  Gln  Ala  Pro  Lys  Gly  Gln  His  Val  Trp  Gln  Arg
               900                     905                     910

Leu  Ser  Val  His  Val  Lys  Thr  Asn  Glu  Thr  Ala  Cys  Asn  Gln  Thr  Ala
               915                     920                     925

Val  Ile  Lys  Pro  Leu  Thr  Lys  Ser  Tyr  Gln  Gly  Ser  Gly  Lys  Ser  Leu
               930                     935                     940

Thr  Phe  Ser  Asp  Ala  Ser  Thr  Lys  Thr  Leu  Tyr  Asn  Val  Glu  Glu  Glu
945                     950                     955                          960

Asp  Asn  Thr  Pro  Ser  Ala  His  Phe  Ser  Pro  Pro  Ser  Ser  Pro  Ser  Met
                    965                     970                     975

Val  Val  His  Arg  Arg  Gly  Pro  Pro  Val  Ala  Thr  Thr  Pro  Pro  Leu  Pro
               980                     985                     990

Pro  His  Leu  Thr  Ala  Glu  Glu  Thr  Pro  Leu  Phe  Leu  Ala  Asp  Ser  Val
               995                     1000                    1005

Ile  Pro  Lys  Gly  Leu  Pro  Pro  Leu  Pro  Gln  Gln  Gln  Pro  Gln  Gln
     1010                    1015                    1020

Pro  Pro  Pro  Gln  Gln  Pro  Pro  Gln  Gln  Pro  Lys  Ser  Leu  Met  Asp  Gln
1025                    1030                    1035                         1040

Leu  Gln  Gly  Val  Val  Thr  Asn  Phe  Gly  Ser  Gly  Ile  Pro  Asp  Phe  His
                    1045                    1050                    1055

Ala  Val  Leu  Ala  Gly  Pro  Gly  Thr  Pro  Gly  Asn  Ser  Leu  Arg  Ser  Leu
               1060                    1065                    1070

Tyr  Pro  Pro  Pro  Pro  Pro  Pro  Gln  His  Leu  Gln  Met  Leu  Pro  Leu  His
                    1075                    1080                    1085

Leu  Ser  Thr  Phe  Gln  Glu  Glu  Ser  Ile  Ser  Pro  Pro  Gly  Glu  Asp  Ile
     1090                    1095                    1100

Asp  Asp  Asp  Ser  Glu  Arg  Phe  Lys  Leu  Leu  Gln  Glu  Phe  Val  Tyr  Glu
1105                    1110                    1115                         1120

Arg  Glu  Gly  Asn  Thr  Glu  Glu  Asp  Glu  Leu  Glu  Glu  Glu  Glu  Asp  Leu
                    1125                    1130                    1135

Pro  Thr  Ala  Ser  Lys  Leu  Thr  Pro  Glu  Asp  Ser  Pro  Ala  Leu  Thr  Pro
               1140                    1145                    1150

Pro  Ser  Pro  Phe  Arg  Asp  Ser  Val  Ala  Ser  Gly  Ser  Ser  Val  Pro  Ser
               1155                    1160                    1165
```

| Ser | Pro | Val | Ser | Glu | Ser | Val | Leu | Cys | Thr | Pro | Pro | Asn | Val | Thr | Tyr |
|---|---|---|---|---|---|---|---|---|---|---|---|---|---|---|---|
| | 1170 | | | | 1175 | | | | | 1180 | | | | | |

| Ala | Ser | Val | Ile | Leu | Arg | Asp | Tyr | Lys | Gln | Ser | Ser | Thr | Leu |
|---|---|---|---|---|---|---|---|---|---|---|---|---|---|
| 1185 | | | | | 1190 | | | | | 1195 | | | |

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC775

( x i ) SEQUENCE DESCRIPTION: SEQ ID NO:3:

GCTAGCATAA CCCCTTGGGG CCTCTAAACG GGTCT      35

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC776

( x i ) SEQUENCE DESCRIPTION: SEQ ID NO:4:

CTCAAGACCC GTTTAGAGGC CCCAAGGGGT TATGCTAGCT GCA      43

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC777

( x i ) SEQUENCE DESCRIPTION: SEQ ID NO:5:

TGAGGGGTTT TTTGCTGAAA GGAGGAACTA TGCGGCCGCA      40

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC778

( x i ) SEQUENCE DESCRIPTION: SEQ ID NO:6:

AGCTTGCGGC CGCATAGTTC CTCCTTTCAG CAAAAAACCC      40

( 2 ) INFORMATION FOR SEQ ID NO:7:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid ( v i i ) IMMEDIATE SOURCE:
    ( B ) CLONE: ZC1751

( x i ) SEQUENCE DESCRIPTION: SEQ ID NO:7:

AATTCTGTGC TCTGTCAAG                                                        19

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC1752

( x i ) SEQUENCE DESCRIPTION: SEQ ID NO:8:

GATCCTTGAC AGAGCACAG                                                        19

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC2063

( x i ) SEQUENCE DESCRIPTION: SEQ ID NO:9:

GATCCAAACT AGTAAAAGAG CT                                                    22

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid ( v i i ) IMMEDIATE SOURCE:
        ( B ) CLONE: ZC2064

( x i ) SEQUENCE DESCRIPTION: SEQ ID NO:10:

CTTTTACTAG TTTG                                                             14

( 2 ) INFORMATION FOR SEQ ID NO:11:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid (v i i) IMMEDIATE SOURCE:
    (B) CLONE: ZC2938

(x i) SEQUENCE DESCRIPTION: SEQ ID NO:11:

GACAGAGCAC AGATTCACTA GTGAGCTCTT TTTTTTTTTT TTT        43

(2) INFORMATION FOR SEQ ID NO:12:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid (v i i) IMMEDIATE SOURCE:
    (B) CLONE: ZC3015

(x i) SEQUENCE DESCRIPTION: SEQ ID NO:12:

TTCCATGGCA CCGTCAAGGC T        21

(2) INFORMATION FOR SEQ ID NO:13:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid (v i i) IMMEDIATE SOURCE:
    (B) CLONE: ZC3016

(x i) SEQUENCE DESCRIPTION: SEQ ID NO:13:

AGTGATGGCA TGGACTGTGG T        21

(2) INFORMATION FOR SEQ ID NO:14:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: other nucleic acid (v i i) IMMEDIATE SOURCE:
    (B) CLONE: ZC3652

(x i) SEQUENCE DESCRIPTION: SEQ ID NO:14:

ACATGCACCA TGCTCTGTGT        20

(2) INFORMATION FOR SEQ ID NO:15:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (i i) MOLECULE TYPE: other nucleic acid (v i i) IMMEDIATE SOURCE:
    (B) CLONE: ZC3654

(x i) SEQUENCE DESCRIPTION: SEQ ID NO:15:

AGTGATGGCA TGGACTGTGG T        21